US008075894B2

(12) United States Patent
Chvatchko

(10) Patent No.: US 8,075,894 B2
(45) Date of Patent: Dec. 13, 2011

(54) USE OF SOLUBLE CD164 IN INFLAMMATORY AND/OR AUTOIMMUNE DISORDERS

(75) Inventor: Yolande Chvatchko, Confignon (CH)

(73) Assignee: Merck Serono SA, Coinsins, Vaud (CH)

( * ) Notice: Subject to any disclaimer, the term of this patent is extended or adjusted under 35 U.S.C. 154(b) by 88 days.

(21) Appl. No.: 12/341,490

(22) Filed: Dec. 22, 2008

(65) Prior Publication Data

US 2009/0285838 A1 Nov. 19, 2009

Related U.S. Application Data

(63) Continuation of application No. 10/565,741, filed as application No. PCT/EP2004/051596 on Jul. 23, 2004, now abandoned.

(30) Foreign Application Priority Data

Jul. 23, 2003 (EP) ..................................... 03077316

(51) Int. Cl.
*A61K 39/00* (2006.01)
(52) U.S. Cl. ............... 424/184.1; 424/185.1; 424/192.1; 514/21.2
(58) Field of Classification Search .......................... None
See application file for complete search history.

(56) References Cited

FOREIGN PATENT DOCUMENTS

EP          1033401 A2    9/2000
WO    WO 02/098917 A2   12/2002

OTHER PUBLICATIONS

Mizuhara et al. Critical involvement of interferon gamma in the pathogenesis of T-cell activation-associated hepatitis and regulatory mechanisms of interleukin-6 for the manifestations of hepatitis. Hepatology. Jun. 1996;23(6):1608-15.*
Attwood TK. Genomics. The Babel of bioinformatics. Science. 290(5491):471-473, 2000.*
Altschul, S.F. et al. "Basic Local Alignment Search Tool," *J. Mol. Biol.*, 1990, pp. 403-410, vol. 215.
Altschul, S.F. et al. "Gapped BLAST and PSI-BLAST: a new generation of protein database search programs," *Nucleic Acids Research*, 1997, pp. 3389-3402, vol. 25, No. 17.
Anthony-Cahill, S.J. and Magliery, T.J. "Expanding the Natural Repertoire of Protein Structure and Function," *Current Pharmaceutical Biotechnology*, 2002, pp. 299-315, vol. 3.
Armaleo, D. et al. "Biolistic nuclear transformation of *Saccharomyces cerevisiae* and other fungi," *Curr Genet*, 1990, pp. 97-103, vol. 17.
Brown, A.R. et al. "The Total Chemical Synthesis of Monocyte Chemotactic Protein-1 (MCP-1)," *Journal of Peptide Science*, 1996, pp. 40-46, vol. 2.
Brutlag, D.L. et al. "Improved sensitivity of biological sequence database searches," *Comput Appl Biosci*, 1990, pp. 237-245, vol. 6, No. 3.

Casi, G. and Hilvert, D. "Convergent protein synthesis," *Current Opinion in Structural Biology*, 2003, pp. 589-594, vol. 13.
Chai, H. et al. "Glycosylation and high-level secretion of human tumour necrosis factor-β in recombinant baculovirus-infected insect cells," *Biotechnol. Appl. Biochem.*, 1993, pp. 259-273, vol. 18.
Chan, J.Y.-H. et al. "Relationship between Novel Isoforms, Functionally Important Domains, and Subcellular Distribution of CD164/Endolyn," *The Journal of Biological Chemistry*, Jan. 19, 2001, pp. 2139-2152, vol. 276, No. 3.
Clark, A.J. "The Mammary Gland as a Bioreactor: Expression, Processing, and Production of Recombinant Proteins," *Journal of Mammary Gland Biology and Neoplasia*, 1998, pp. 337-350, vol. 3, No. 3.
Cleland, J.L. "The Development of Stable Protein Formulations: A Close Look at Protein Aggregation, Deamidation, and Oxidation," *Critical Reviews in Therapeutic Drug Carrier Systems*, 1993, pp. 307-377, vol. 10, No. 4.
Cleland, J.L. "Emerging protein delivery methods," *Current Opinion in Biotechnology*, 2001, pp. 212-219, vol. 12.
Cunningham, B.C. and Wells, J.A. "High-Resolution Epitope Mapping of hGH-Receptor Interactions by Alanine-Scanning Mutagenesis," *Science*, Jun. 2, 1989, pp. 1081-1085, vol. 244.
Dougherty, D.A. "Unnatural amino acids as probes of protein structure and function," *Current Opinion in Chemical Biology*, 2000, pp. 645-652, vol. 4.
Doyonnas, R. et al. "CD164 Monoclonal Antibodies That Block Hemopoietic Progenitor Cell Adhesion and Proliferation Interact with the First Mucin Domain of the CD164 Receptor," *The Journal of Immunology*, 2000, pp. 840-851, vol. 165.
Feldman, L.J. "Adenovirus-mediated arterial gene therapy for restenosis: problems and perspectives," *Semin Intervent Cardiol*, 1996, pp. 203-208, vol. 1.
Gendel, S.M. "Sequence Analysis for Assessing Potential Allergenicity," *Annals New York Academy of Sciences*, 2002, pp. 87-98, vol. 964.
Gentz, R. "Bioassay for trans-activation using purified human immunodeficiency virus *tat*-encoded protein: Trans-activation requires mRNA synthesis," *Proc. Natl. Acad. Sci. USA*, Feb. 1989, pp. 821-824, vol. 86.
Gish, W. and States, D.J. "Identification of protein coding regions by database similarity search," *Nature Genetics*, Mar. 1993, pp. 266-272, vol. 3.
Golebiowski, A. et al. "High-throughput organic synthesis of peptide mimetics," *Current Opinion in Drug Discovery and Development*, 2001, pp. 428-434, vol. 4, No. 4.
Gonnet, G.H. et al. "Exhaustive Matching of the Entire Protein Sequence Database," *Science*, Jun. 5, 1992, pp. 1443-1445, vol. 256.
Gor, D.O. et al. "$T_H1$-$T_H2$: a Procrustean paradigm," *Nature Immunology*, Jun. 2003, pp. 503-505, vol. 4, No. 6.
Graddis, T.J. et al. "Designing Proteins That Work Using Recombinant Technologies," *Current Pharmaceutical Biotechnology*, 2002, pp. 285-297, vol. 3.
Gustafsson, C. et al. "Codon bias and heterologous protein expression," *TRENDS in Biotechnology*, Jul. 2004, pp. 346-353, vol. 22, No. 7.
Henikoff, S. and Henikoff, J.G. "Performance Evaluation of Amino Acid Substitution Matrices," *Proteins: Structure, Function, and Genetics*, 1993, pp. 49-61, vol. 17.

(Continued)

*Primary Examiner* — Maher Haddad
(74) *Attorney, Agent, or Firm* — Saliwanchik, Lloyd & Eisenschenk

(57) ABSTRACT

The present invention relates to novel therapeutic uses of soluble proteins comprising the extracellular region of human CD164, in particular for treating inflammatory and/or autoimmune disorders.

13 Claims, 7 Drawing Sheets

OTHER PUBLICATIONS

Herrick, C.A. and Bottomly, K. "To Respond or Not to Respond: T Cells in Allergic Asthma," *Nat Rev Immunol*, May 2003, pp. 405-412, vol. 3.

Higgins, D.G. et al. "Using CLUSTAL for Multiple Sequence Alignments," *Methods in Enzymology*, 1996, pp. 383-402, vol. 266.

Hruby, V.J. and Balse, P.M. "Conformational and Topographical Considerations in Designing Agonist Peptidomimetics from Peptide Leads," *Current Medicinal Chemistry*, 2000, pp. 945-970, vol. 7.

Karlin, S. and Altschul, S.F. "Methods for assessing the statistical significance of molecular sequence features by using general scoring schemes," *Proc Natl Acad Sci USA*, Mar. 1990, pp. 2264-2268, vol. 87.

Lee, Y.-N. et al. "Identification of a Role for the Sialomucin CD164 in Myogenic Differentiation by Signal Sequence Trapping in Yeast," *Molecular and Cellular Biology*, Nov. 2001, pp. 7696-7706, vol. 21, No. 22.

Lenhard, T. et al. "A new set of versatile vectors for the heterologous expression of foreign genes using the baculovirus system," *Gene*, 1996, pp. 187-190, vol. 169.

Luo, Y. and Prestwich, G. "Novel biomaterials for drug delivery," *Expert Opin. Ther. Patents*, 2001, pp. 1395-1410, vol. 11, No. 9.

Malik, F. et al. "Polyethylene Glycol (PEG)-modified Granulocyte-Macrophage Colony-stimulating Factor (GM-CSF) with Conserved Biological Activity," *Exp. Hematol.*, 1992, pp. 1028-1035, vol. 20.

Marshall, S.A. et al. "Rational design and engineering of therapeutic proteins," *Drug Discov Today*, Mar. 2003, pp. 212-221, vol. 8, No. 5.

Matsui, T. et al. "The Ratio of Splicing Variants of MGC-24/CD164, a Sialomucin, Correlates with the Metastatic Potential of Colorectal Carcinomas," *J. Biochem*, 2000, pp. 1103-1107, vol. 127, No. 6.

Muir, T.W. "Semisynthesis of Proteins by Expressed Protein Ligation," *Annu. Rev. Biochem.*, 2003, pp. 249-289, vol. 72.

Murphy, L.R. et al. "Simplified amino acid alphabets for protein fold recognition and implications for folding," *Protein Engineering*, 2000, pp. 149-152, vol. 13, No. 3.

Nicolau, C. et al. "Liposomes as Carriers for in Vivo Gene Transfer and Expression," *Methods in Enzymology*, 1987, pp. 157-176, vol. 149.

Ohno, T. et al. "Gene Therapy for Vascular Smooth Muscle Cell Proliferation After Arterial Injury," *Science*, Aug. 5, 1994, pp. 781-784, vol. 265.

Pearson, W.R. and Lipman, D.J. "Improved tools for biological sequence comparison," *Proc Natl Acad Sci USA*, Apr. 1988, pp. 2444-2448, vol. 85.

Pillai, O. and Panchagnula, R. "Polymers in drug delivery," *Current Opinion in Chemical Biology*, 2001, pp. 447-451, vol. 5.

Rogov, S.I. and Nekrasov, A.N. "A numerical measure of amino acid residues similarity based on the analysis of their surroundings in natural protein sequences," *Protein Engineering*, 2001, pp. 459-463, vol. 14, No. 7.

Schellekens, H. "Bioequivalence and the Immunogenicity of Biopharmaceuticals," *Nat Rev Drug Discov*, Jun. 2002, pp. 457-462, vol. 1.

Smith, G.E. et al. "Production of Human Beta Interferon in Insect Cells Infected with a Baculovirus Expression Vector," *Molecular and Cellular Biology*, Dec. 1983, pp. 2156-2165, vol. 3, No. 12.

Tascon, R.E. et al. "Vaccination against tuberculosis by DNA injection," *Nature Medicine*, Aug. 1996, pp. 888-892, vol. 2, No. 8.

Terpe, K. "Overview of tag protein fusions: from molecular and biochemical fundamentals to commercial systems," *Appl Microbiol Biotechnol*, 2003, pp. 523-533, vol. 60.

Thompson, J.D. et al. "Clustal W: improving the sensitivity of progressive multiple sequence alignment through sequence weighting, position-specific gap penalties and weight matrix choice," *Nucleic Acids Research*, 1994, pp. 4673-4680, vol. 22, No. 22.

Tutuncu, Z. et al. "Anti-TNF therapy for other inflammatory conditions," *Clin Exp Rheumatol*, 2002, pp. S146-S151, vol. 20 (Suppl 28).

Vasserot, A.P. et al. "Optimization of protein therapeutics by directed evolution," *Drug Discov Today*, Feb. 2003, pp. 118-126, vol. 8, No. 3.

Villain, M. et al. "Covalent capture: a new tool for the purification of synthetic and recombinant polypeptides," *Chemistry and Biology*, 2001, pp. 673-679, vol. 8.

Vlasak, R. et al. "Nucleotide sequence of cloned cDNA coding for honeybee prepromelittin," *Eur. J. Biochem*, 1983, pp. 123-126, vol. 135.

Watt, S.M. et al. "Functionally defined CD164 epitopes are expressed on CD344[30] cells throughout ontogeny but display distinct distribution patterns in adult hematopoietic and nonhematopoietic tissues," *Blood*, May 15, 2000, pp. 3113-3124, vol. 95, No. 10.

Watt, S.M. and Chan, J.Y. "CD164-A Novel Sialomucin on CD34[+] Cells," *Leukemia and Lymphoma*, 2000, pp. 1-25, vol. 37, Nos. 1-2.

Wilson, I.A., et al. "The Structure of an Antigenic Determinant in a Protein," *Cell*, Jul. 1984, pp. 767-778, vol. 37.

Wong, T.-K. et al. "Appearance of β-lactamase activity in animal cells upon liposome-mediated gene transfer," *Gene*, 1980, pp. 87-94, vol. 10.

Zannettino, A.C.W. et al. "The Sialomucin CD164 (MGC-24v) Is an Adhesive Glycoprotein Expressed by Human Hematopoietic Progenitors and Bone Marrow Stromal Cells That Serves as a Potent Negative Regulator of Hematopoiesis," *Blood*, Oct. 15, 1998, pp. 2613-2628, vol. 92, No. 8.

Zannettino, A.C.W. "CD164," *J Biol Regul Homeostat Agents*, 2001, pp. 394-396, vol. 15.

Baker, D. et. al. "Models of Multiple Sclerosis" *Advances in Clinical Neuroscience and Rehabilitation*, Jan./Feb. 2007, pp. 10-12, vol. 6, No. 6.

Sriram, M-D. et al. "Experimental Allergic Encephalomyelitis: A Misleading Model of Multiple Sclerosis" *Annals of Neurology*, Dec. 2005, pp. 939-945, vol. 58, No. 6, Wiley-Liss, Inc.

Steinman, M-D. et al. "How to Successfully Apply Animal Studies in Experimental Allergic Encephalomyelitis to Research on Multiple Sclerosis" *Annals of Neurology*, Jul. 2006, pp. 12-21, vol. 60, No. 1, Wiley-Liss, Inc.

Wiendl, H. et al. "Therapeutic approaches in multiple sclerosis: lessons from failed and interrupted treatment trials" *BioDrugs* 2002, pp. 183-200, vol. 16, No. 3.

'T Hart, B.A. et al. "Evaluating the validity of animal models for research into therapies for immune-based disorders" *Drug Discov Today* Jun. 15, 2004, pp. 517-524, vol. 9, No. 12.

\* cited by examiner

```
hCD164        MSRLSRSLLWAATCLGVLCVLSA DKNTTQHPNVTTLAPISNVTSAPVTSLPLVTTPAP
hCD164-DELTA4 MSRLSRSLLWAATCLGVLCVLSA DKNTTQHPNVTTLAPISNVTSAPVTSLPLVTTPAP
hCD164-DELTA5 MSRLSRSLLWAATCLGVLCVLSA DKNTTQHPNVTTLAPISNVTSAPVTSLPLVTTPAP
hMGC-24       MSRLSRSLLWAATCLGVLCVLSA DKNTTQHPNVTTLAPISNVTSAPVTSLPLVTTPAP
                                        *     *                  ** hCD164        ETCEGRNSCVSCFNVSVVNTTCFWIECKDESYCSHNSTVSDCQVGNTTDFCSVSTATP
hCD164-DELTA4 ETCEGRNSCVSCFNVSVVNTTCFWIECKDESYCSHNSTVSDCQVGNTTDFCS------
hCD164-DELTA5 ETCEGRNSCVSCFNVSVVNTTCFWIECKDESYCSHNSTVSDCQVGNTTDFCSVSTATP
hMGC-24       ETCEGRNSCVSCFNVSVVNTTCFWIECKDESYCSHNSTVSDCQVGNTTDFCSVSTATP
                     *      *                *                     ** * hCD164        VPTANSTAKPTVQPSPSTTSKTVTTSGTTNNTVTPTSQPVRKSTFDAASFIGGIVLVL
hCD164-DELTA4 -------AKPTVQPSPSTTSKTVTTSGTTNNTVTPTSQPVRKSTFDAASFIGGIVLVL
hCD164-DELTA5 VPTANST------------------GTTNNTVTPTSQPVRKSTFDAASFIGGIVLVL
hMGC-24       VPTANSTAKPTVQPSPSTTSKTVTTSGTTNNTVTPTSQPVRKSTFDAASFIGGIVLVL
                * ***      *    *  ****  *  * *   *   **              *     ↑ hCD164        GVQAVIFFLYKFCKSKERNYHTL
hCD164-DELTA4 GVQAVIFFLYKFCKSKERNYHTL
hCD164-DELTA5 GVQAVIFFLYKFCKSKERNYHTL
hMGC-24       EIRCHTRNYIPDLKK
```

B)

```
hMGC-24       DKNTTQHPNVTTLAPISNVTSAPVTSLPLVTTPAPETCEGRNSCVSCFNVSVVNTTCFWI
hCD164-DELTA5 DKNTTQHPNVTTLAPISNVTSAPVTSLPLVTTPAPETCEGRNSCVSCFNVSVVNTTCFWI
hCD164-DELTA4 DKNTTQHPNVTTLAPISNVTSAPVTSLPLVTTPAPETCEGRNSCVSCFNVSVVNTTCFWI
SEQ ID NO: 1  DKNTTQHPNVTTLAPISNVTSAPVTSLPLVTTPAPETCEGRNSCVSCFNVSVVNTTCFWI
SEQ ID NO: 7852 DKNTTQHPNVTTLAPISNVTSAPVTSLPLVTTPAPETCEGRNSCVSCFNVSVVNTTCFWI
NOV25         DKNTTQHPNVTTLAPISNVKSLISCISPPNS---PETCEGRNSCVSCFNVSVVNTTCFWI hMGC-24       ECK--DESYCSHNSTVSDCQVGNTTDFCSVSTATPVPTANSTAKPTVQPSPSTTSKTVTT
hCD164-DELTA5 ECK--DESYCSHNSTVSDCQVGNTTDFCSVSTATPVPTANST------------------
hCD164-DELTA4 ECK--DESYCSHNSTVSDCQVGNTTDFCS-------------AKPTVQPSPSTTSKTVTT
SEQ ID NO: 1  ECK--DESYCSHNSTVSDCQVGNTTDFCSVSTATPVPTANSTAKPTVQPSPSTTSKTVTT
SEQ ID NO: 7852 ECK--DESYCSHNSTVSDCQVGNTTDFCSVSTATPVPTANSTAKPTVQPSPSTTSKTVTT
NOV25         ECPPTDESYCSHNSTVSDCQVGNTTDFCSGKYSYWLLGSIP-AKPTVQPSPSTTSKTVTT hMGC-24       SGTTNNTVTPTSQPVRKSTFDA
hCD164-DELTA5 -GTTNNTVTPTSQPVRKSTFDA
hCD164-DELTA4 SGTTNNTVTPTSQPVRKSTFDA
SEQ ID NO: 1  SGTTNNTVTPTSQPVRKSTFDA
SEQ ID NO: 7852 SGTTNNTVTPTSQPVRKSTFDA
NOV25         SGTTNNTVTPTSQPVRKSTFDA
```

Figure 2
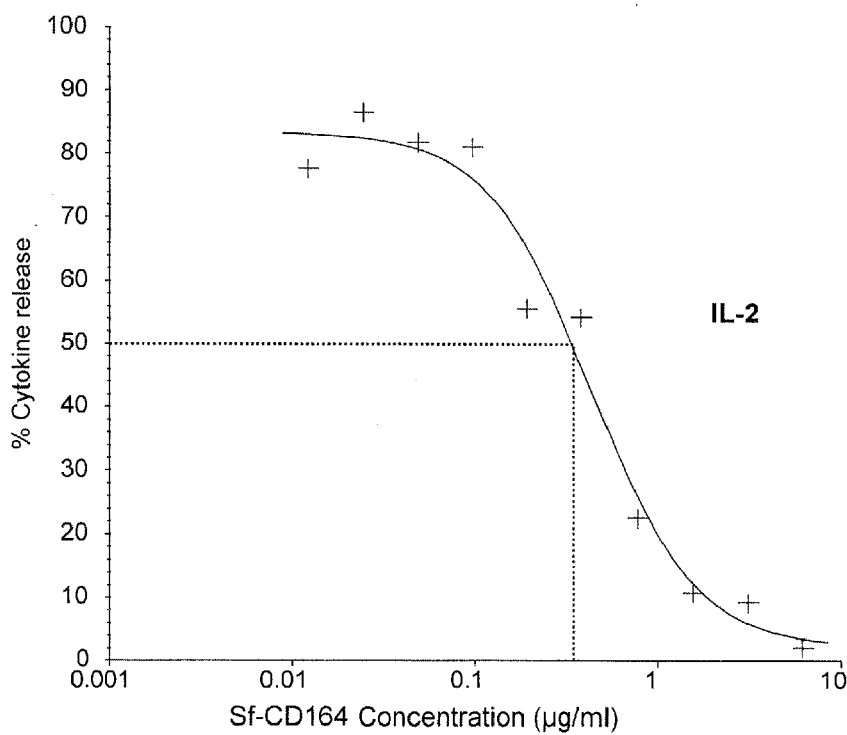
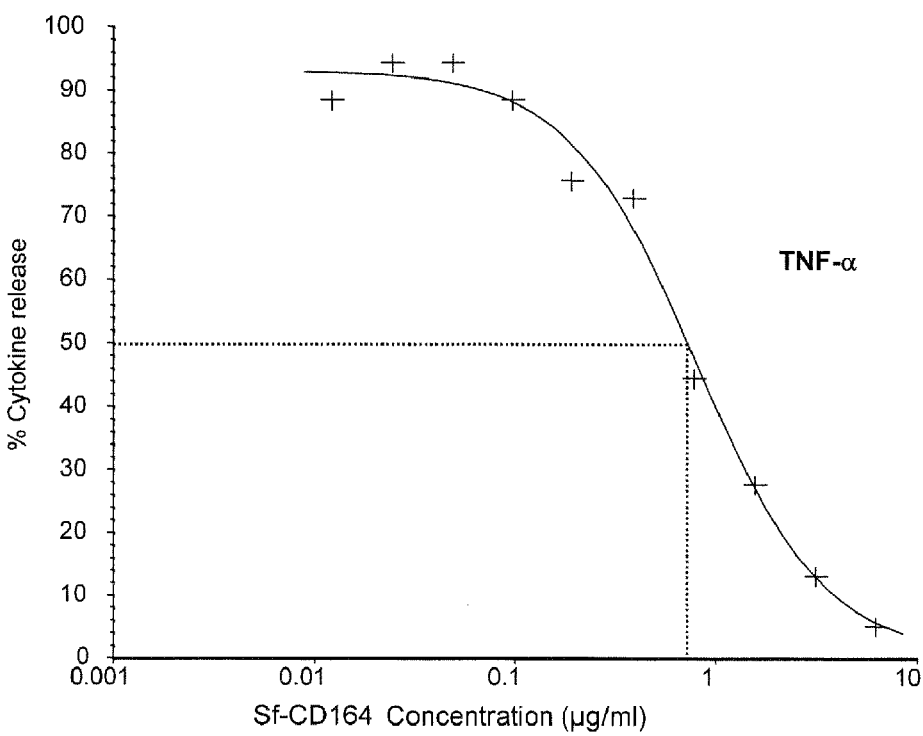

Figure 3
A)
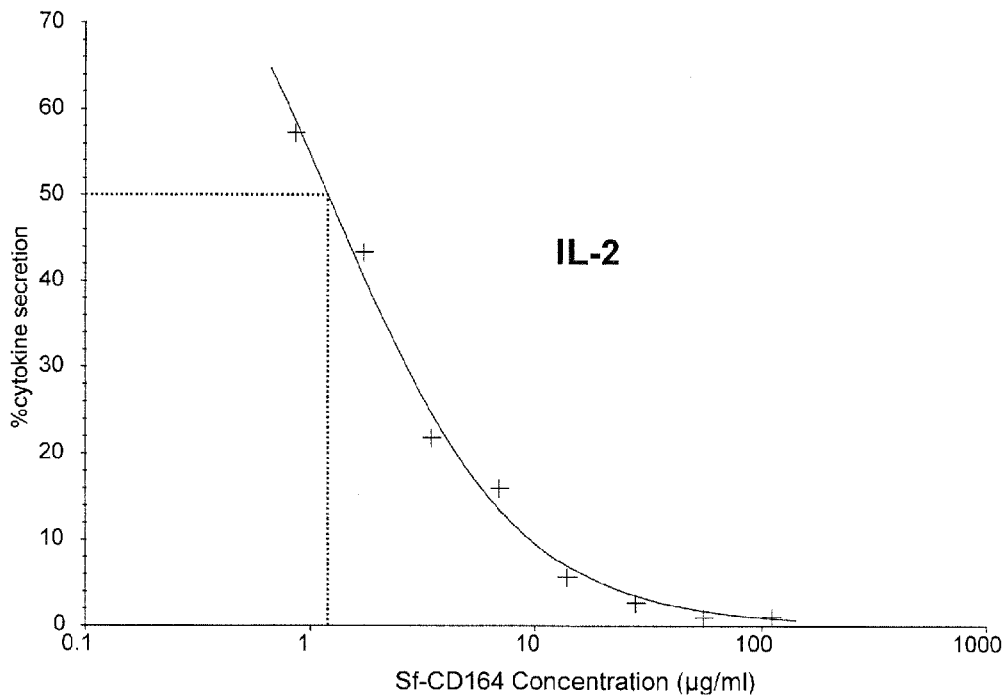
B)
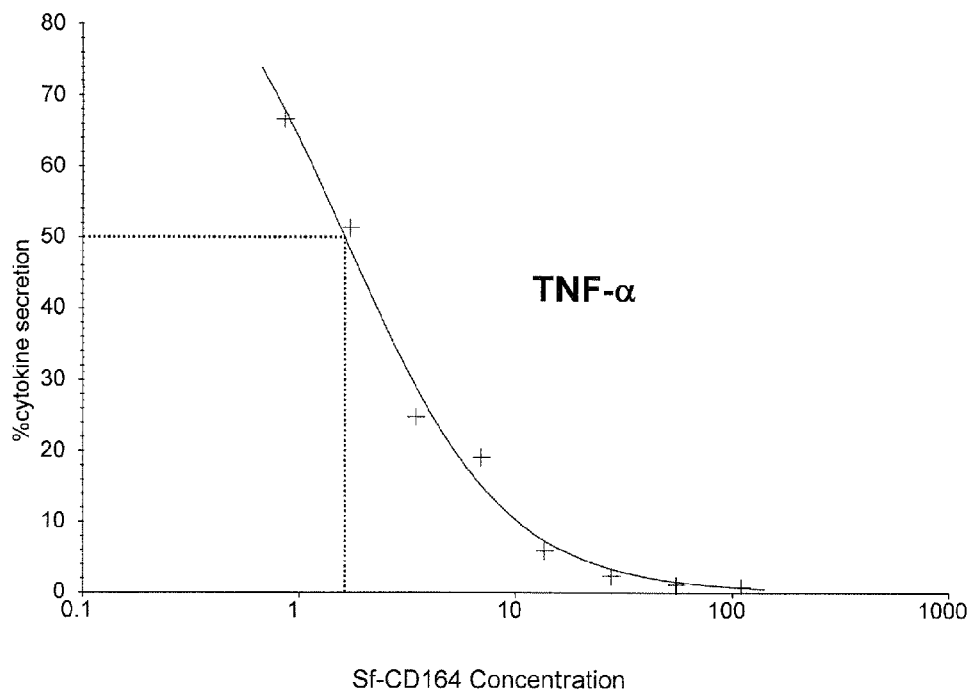

Figure 5
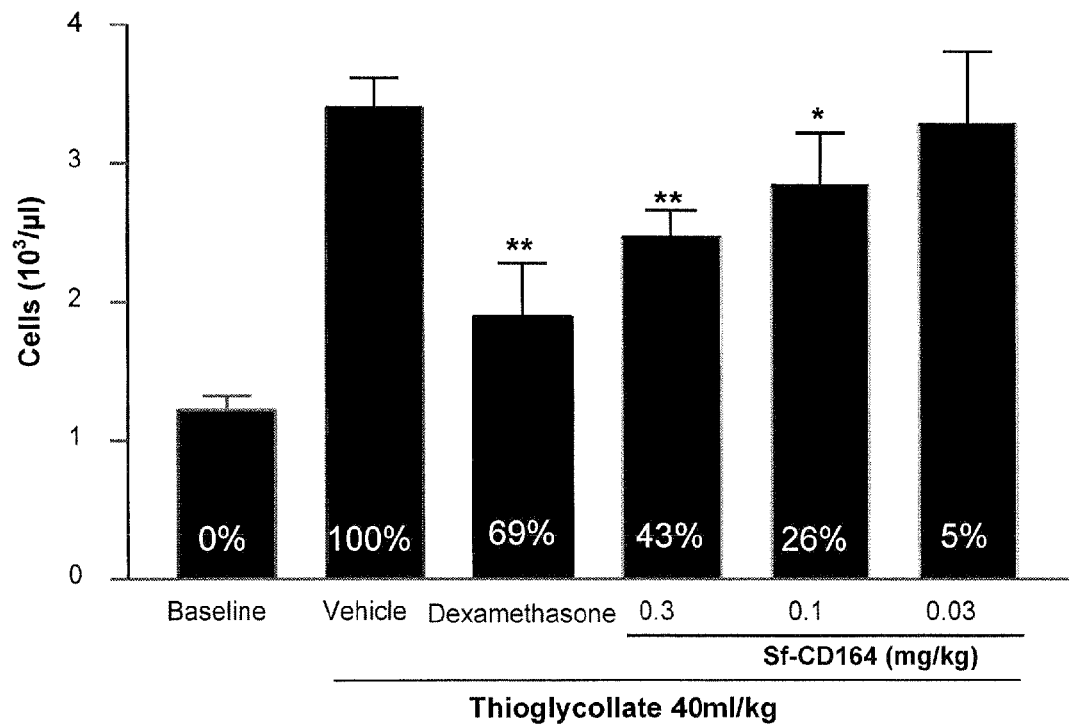
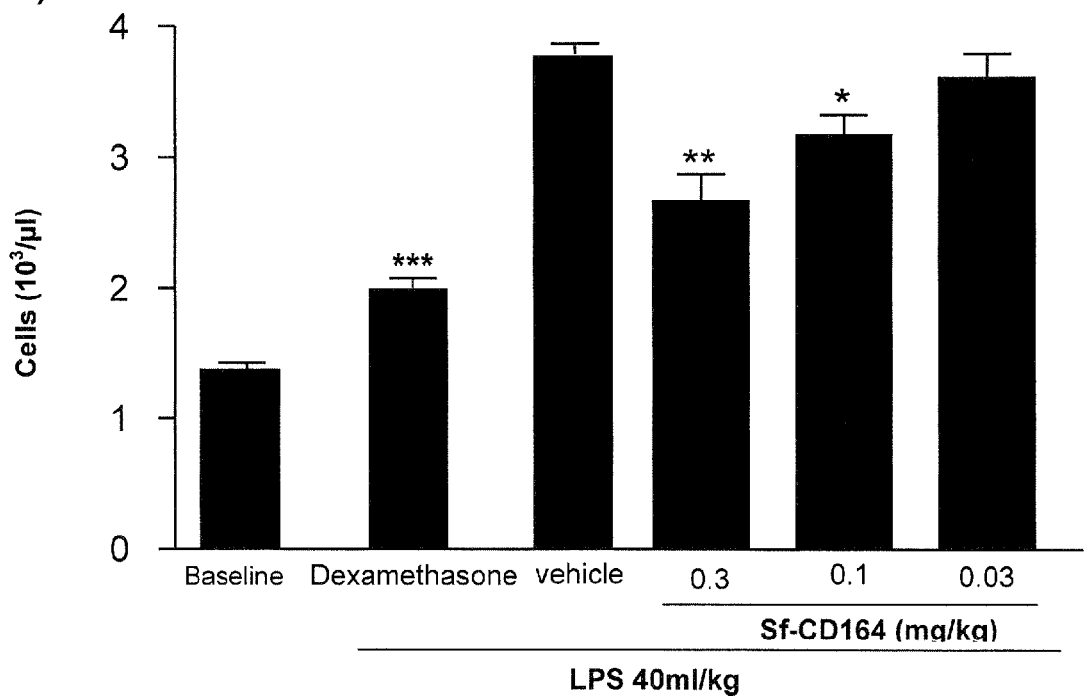

SEQUENCE LISTING

```
<160> NUMBER OF SEQ ID NOS: 9

<210> SEQ ID NO 1
<211> LENGTH: 140
<212> TYPE: PRT
<213> ORGANISM: homo sapiens
<220> FEATURE:
<221> NAME/KEY: PUTATIVE-MUCIN-CORE-PROTEIN-24
<222> LOCATION: (1)..(140)
<220> FEATURE:
<221> NAME/KEY: N-LINKED-GLCNAC
<222> LOCATION: (3)..(3)
<220> FEATURE:
<221> NAME/KEY: N-LINKED-GLCNAC
<222> LOCATION: (9)..(9)
<220> FEATURE:
<221> NAME/KEY: O-LINKED
<222> LOCATION: (11)..(11)
<220> FEATURE:
<221> NAME/KEY: O-LINKED
<222> LOCATION: (12)..(12)
<220> FEATURE:
<221> NAME/KEY: O-LINKED
<222> LOCATION: (17)..(17)
<220> FEATURE:
<221> NAME/KEY: N-LINKED-GLCNAC
<222> LOCATION: (18)..(18)
<220> FEATURE:
<221> NAME/KEY: O-LINKED
<222> LOCATION: (20)..(20)
<220> FEATURE:
<221> NAME/KEY: O-LINKED
<222> LOCATION: (21)..(21)
<220> FEATURE:
<221> NAME/KEY: O-LINKED
<222> LOCATION: (25)..(25)
<220> FEATURE:
<221> NAME/KEY: O-LINKED
<222> LOCATION: (26)..(26)
<220> FEATURE:
<221> NAME/KEY: O-LINKED
<222> LOCATION: (31)..(31)
<220> FEATURE:
<221> NAME/KEY: O-LINKED
<222> LOCATION: (32)..(32)
<220> FEATURE:
<221> NAME/KEY: N-LINKED-GLCNAC
<222> LOCATION: (49)..(49)
<220> FEATURE:
<221> NAME/KEY: N-LINKED-GLCNAC
<222> LOCATION: (54)..(54)
<220> FEATURE:
<221> NAME/KEY: N-LINKED-GLCNAC
<222> LOCATION: (71)..(71)
<220> FEATURE:
<221> NAME/KEY: CK2-PHOSPHO-SITE
<222> LOCATION: (73)..(76)
<220> FEATURE:
<221> NAME/KEY: N-LINKED-GLCNAC
<222> LOCATION: (81)..(81)
<220> FEATURE:
<221> NAME/KEY: O-LINKED
<222> LOCATION: (89)..(89)
<220> FEATURE:
<221> NAME/KEY: O-LINKED
<222> LOCATION: (90)..(90)
<220> FEATURE:
<221> NAME/KEY: O-LINKED
<222> LOCATION: (92)..(92)
<220> FEATURE:
<221> NAME/KEY: O-LINKED
<222> LOCATION: (96)..(96)
<220> FEATURE:
<221> NAME/KEY: N-LINKED-GLCNAC
<222> LOCATION: (98)..(98)
<220> FEATURE:
<221> NAME/KEY: O-LINKED
```

```
<222> LOCATION: (99)..(99)
<220> FEATURE:
<221> NAME/KEY: O-LINKED
<222> LOCATION: (100)..(100)
<220> FEATURE:
<221> NAME/KEY: PKC-PHOSPHO-SITE
<222> LOCATION: (100)..(102)
<220> FEATURE:
<221> NAME/KEY: O-LINKED
<222> LOCATION: (104)..(104)
<220> FEATURE:
<221> NAME/KEY: O-LINKED
<222> LOCATION: (108)..(108)
<220> FEATURE:
<221> NAME/KEY: O-LINKED
<222> LOCATION: (110)..(110)
<220> FEATURE:
<221> NAME/KEY: O-LINKED
<222> LOCATION: (111)..(111)
<220> FEATURE:
<221> NAME/KEY: O-LINKED
<222> LOCATION: (112)..(112)
<220> FEATURE:
<221> NAME/KEY: PKC-PHOSPHO-SITE
<222> LOCATION: (112)..(114)
<220> FEATURE:
<221> NAME/KEY: O-LINKED
<222> LOCATION: (113)..(113)
<220> FEATURE:
<221> NAME/KEY: O-LINKED
<222> LOCATION: (115)..(115)
<220> FEATURE:
<221> NAME/KEY: O-LINKED
<222> LOCATION: (117)..(117)
<220> FEATURE:
<221> NAME/KEY: O-LINKED
<222> LOCATION: (118)..(118)
<220> FEATURE:
<221> NAME/KEY: O-LINKED-GLYCOSAMINOGLYCAN
<222> LOCATION: (119)..(119)
<220> FEATURE:
<221> NAME/KEY: MYRISTYL
<222> LOCATION: (120)..(125)
<220> FEATURE:
<221> NAME/KEY: O-LINKED
<222> LOCATION: (121)..(121)
<220> FEATURE:
<221> NAME/KEY: O-LINKED
<222> LOCATION: (122)..(122)
<220> FEATURE:
<221> NAME/KEY: N-LINKED-GLCNAC
<222> LOCATION: (123)..(123)
<220> FEATURE:
<221> NAME/KEY: O-LINKED
<222> LOCATION: (125)..(125)
<220> FEATURE:
<221> NAME/KEY: O-LINKED
<222> LOCATION: (127)..(127)
<220> FEATURE:
<221> NAME/KEY: O-LINKED
<222> LOCATION: (129)..(129)
<220> FEATURE:
<221> NAME/KEY: O-LINKED
<222> LOCATION: (130)..(130)
<220> FEATURE:
<221> NAME/KEY: CAMP-PHOSPHO-SITE
<222> LOCATION: (134)..(137)
<220> FEATURE:
<221> NAME/KEY: O-LINKED
<222> LOCATION: (136)..(136)
<220> FEATURE:
<221> NAME/KEY: CK2-PHOSPHO-SITE
<222> LOCATION: (136)..(139)

<400> SEQUENCE: 1

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
```

```
                    20                  25                  30
Pro Ala Pro Glu Thr Cys Glu Gly Arg Asn Ser Cys Val Ser Cys Phe
            35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Val Ser Thr Ala Thr Pro Val Pro Thr
                85                  90                  95

Ala Asn Ser Thr Ala Lys Pro Thr Val Gln Pro Ser Pro Ser Thr Thr
            100                 105                 110

Ser Lys Thr Val Thr Thr Ser Gly Thr Thr Asn Asn Thr Val Thr Pro
        115                 120                 125

Thr Ser Gln Pro Val Arg Lys Ser Thr Phe Asp Ala
        130                 135                 140

<210> SEQ ID NO 2
<211> LENGTH: 146
<212> TYPE: PRT
<213> ORGANISM: homo sapiens

<400> SEQUENCE: 2

Asp Lys Asn Thr Thr Gln His Pro Asn Val Thr Thr Leu Ala Pro Ile
1               5                   10                  15

Ser Asn Val Thr Ser Ala Pro Val Thr Ser Leu Pro Leu Val Thr Thr
            20                  25                  30

Pro Ala Pro Glu Thr Cys Glu Gly Arg Asn Ser Cys Val Ser Cys Phe
            35                  40                  45

Asn Val Ser Val Val Asn Thr Thr Cys Phe Trp Ile Glu Cys Lys Asp
    50                  55                  60

Glu Ser Tyr Cys Ser His Asn Ser Thr Val Ser Asp Cys Gln Val Gly
65                  70                  75                  80

Asn Thr Thr Asp Phe Cys Ser Val Ser Thr Ala Thr Pro Val Pro Thr
                85                  90                  95

Ala Asn Ser Thr Ala Lys Pro Thr Val Gln Pro Ser Pro Ser Thr Thr
            100                 105                 110

Ser Lys Thr Val Thr Thr Ser Gly Thr Thr Asn Asn Thr Val Thr Pro
        115                 120                 125

Thr Ser Gln Pro Val Arg Lys Ser Thr Phe Asp Ala His His His His
        130                 135                 140

His His
145

<210> SEQ ID NO 3
<211> LENGTH: 197
<212> TYPE: PRT
<213> ORGANISM: homo sapiens

<400> SEQUENCE: 3

Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
            35                  40                  45

Ser Leu Pro Leu Val Thr Thr Pro Ala Pro Glu Thr Cys Glu Gly Arg
    50                  55                  60
```

```
Asn Ser Cys Val Ser Cys Phe Asn Val Ser Val Val Asn Thr Thr Cys
 65                  70                  75                  80

Phe Trp Ile Glu Cys Lys Asp Glu Ser Tyr Cys Ser His Asn Ser Thr
                 85                  90                  95

Val Ser Asp Cys Gln Val Gly Asn Thr Thr Asp Phe Cys Ser Val Ser
            100                 105                 110

Thr Ala Thr Pro Val Pro Thr Ala Asn Ser Thr Ala Lys Pro Thr Val
        115                 120                 125

Gln Pro Ser Pro Ser Thr Thr Ser Lys Thr Val Thr Thr Ser Gly Thr
    130                 135                 140

Thr Asn Asn Thr Val Thr Pro Thr Ser Gln Pro Val Arg Lys Ser Thr
145                 150                 155                 160

Phe Asp Ala Ala Ser Phe Ile Gly Gly Ile Val Leu Val Leu Gly Val
                165                 170                 175

Gln Ala Val Ile Phe Phe Leu Tyr Lys Phe Cys Lys Ser Lys Glu Arg
            180                 185                 190

Asn Tyr His Thr Leu
            195

<210> SEQ ID NO 4
<211> LENGTH: 184
<212> TYPE: PRT
<213> ORGANISM: homo sapiens

<400> SEQUENCE: 4

Met Ser Arg Leu Ser Arg Ser Leu Leu Trp Ala Ala Thr Cys Leu Gly
  1               5                  10                  15

Val Leu Cys Val Leu Ser Ala Asp Lys Asn Thr Thr Gln His Pro Asn
                 20                  25                  30

Val Thr Thr Leu Ala Pro Ile Ser Asn Val Thr Ser Ala Pro Val Thr
             35                  40                  45

Ser Leu Pro Leu Val Thr Thr Pro Ala Pro Glu Thr Cys Glu Gly Arg
     50                  55                  60

Asn Ser Cys Val Ser Cys Phe Asn Val Ser Val Val Asn Thr Thr Cys
 65                  70                  75                  80

Phe Trp Ile Glu Cys Lys Asp Glu Ser Tyr Cys Ser His Asn Ser Thr
                 85                  90                  95

Val Ser Asp Cys Gln Val Gly Asn Thr Thr Asp Phe Cys Ser Ala Lys
            100                 105                 110

Pro Thr Val Gln Pro Ser Pro Ser Thr Thr Ser Lys Thr Val Thr Thr
        115                 120                 125

Ser Gly Thr Thr Asn Asn Thr Val Thr Pro Thr Ser Gln Pro Val Arg
    130                 135                 140

Lys Ser Thr Phe Asp Ala Ala Ser Phe Ile Gly Gly Ile Val Leu Val
145                 150                 155                 160

Leu Gly Val Gln Ala Val Ile Phe Phe Leu Tyr Lys Phe Cys Lys Ser
                165                 170                 175

Lys Glu Arg Asn Tyr His Thr Leu
            180

<210> SEQ ID NO 5
<211> LENGTH: 178
<212> TYPE: PRT
<213> ORGANISM: homo sapiens

<400> SEQUENCE: 5
```

```
Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
            35                  40                  45

Ser Leu Pro Leu Val Thr Thr Pro Ala Pro Glu Thr Cys Glu Gly Arg
50                  55                  60

Asn Ser Cys Val Ser Cys Phe Asn Val Ser Val Asn Thr Thr Cys
65                  70                  75                  80

Phe Trp Ile Glu Cys Lys Asp Glu Ser Tyr Cys Ser His Asn Ser Thr
                85                  90                  95

Val Ser Asp Cys Gln Val Gly Asn Thr Thr Asp Phe Cys Ser Val Ser
            100                 105                 110

Thr Ala Thr Pro Val Pro Thr Ala Asn Ser Thr Gly Thr Thr Asn Asn
            115                 120                 125

Thr Val Thr Pro Thr Ser Gln Pro Val Arg Lys Ser Thr Phe Asp Ala
            130                 135                 140

Ala Ser Phe Ile Gly Gly Ile Val Leu Val Leu Gly Val Gln Ala Val
145                 150                 155                 160

Ile Phe Phe Leu Tyr Lys Phe Cys Lys Ser Lys Glu Arg Asn Tyr His
                165                 170                 175

Thr Leu

<210> SEQ ID NO 6
<211> LENGTH: 189
<212> TYPE: PRT
<213> ORGANISM: homo sapiens
<220> FEATURE:
<221> NAME/KEY: SIGNAL
<222> LOCATION: (1)..(23)
<220> FEATURE:
<221> NAME/KEY: PUTATIVE-MUCIN-CORE-PROTEIN-24
<222> LOCATION: (24)..(189)
<220> FEATURE:
<221> NAME/KEY: N-LINKED-GLCNAC
<222> LOCATION: (26)..(26)
<220> FEATURE:
<221> NAME/KEY: N-LINKED-GLCNAC
<222> LOCATION: (32)..(32)
<220> FEATURE:
<221> NAME/KEY: O-LINKED
<222> LOCATION: (34)..(34)
<220> FEATURE:
<221> NAME/KEY: O-LINKED
<222> LOCATION: (35)..(35)
<220> FEATURE:
<221> NAME/KEY: O-LINKED
<222> LOCATION: (40)..(40)
<220> FEATURE:
<221> NAME/KEY: N-LINKED-GLCNAC
<222> LOCATION: (41)..(41)
<220> FEATURE:
<221> NAME/KEY: O-LINKED
<222> LOCATION: (43)..(43)
<220> FEATURE:
<221> NAME/KEY: O-LINKED
<222> LOCATION: (44)..(44)
<220> FEATURE:
<221> NAME/KEY: O-LINKED
<222> LOCATION: (48)..(48)
<220> FEATURE:
<221> NAME/KEY: O-LINKED
<222> LOCATION: (49)..(49)
<220> FEATURE:
<221> NAME/KEY: O-LINKED
<222> LOCATION: (54)..(54)
<220> FEATURE:
```

```
<221> NAME/KEY: O-LINKED
<222> LOCATION: (55)..(55)
<220> FEATURE:
<221> NAME/KEY: N-LINKED-GLCNAC
<222> LOCATION: (72)..(72)
<220> FEATURE:
<221> NAME/KEY: N-LINKED-GLCNAC
<222> LOCATION: (77)..(77)
<220> FEATURE:
<221> NAME/KEY: N-LINKED-GLCNAC
<222> LOCATION: (94)..(94)
<220> FEATURE:
<221> NAME/KEY: N-LINKED-GLCNAC
<222> LOCATION: (104)..(104)
<220> FEATURE:
<221> NAME/KEY: O-LINKED
<222> LOCATION: (112)..(112)
<220> FEATURE:
<221> NAME/KEY: O-LINKED
<222> LOCATION: (113)..(113)
<220> FEATURE:
<221> NAME/KEY: O-LINKED
<222> LOCATION: (115)..(115)
<220> FEATURE:
<221> NAME/KEY: O-LINKED
<222> LOCATION: (119)..(119)
<220> FEATURE:
<221> NAME/KEY: N-LINKED-GLCNAC
<222> LOCATION: (121)..(121)
<220> FEATURE:
<221> NAME/KEY: O-LINKED
<222> LOCATION: (122)..(122)
<220> FEATURE:
<221> NAME/KEY: O-LINKED
<222> LOCATION: (123)..(123)
<220> FEATURE:
<221> NAME/KEY: O-LINKED
<222> LOCATION: (127)..(127)
<220> FEATURE:
<221> NAME/KEY: O-LINKED
<222> LOCATION: (131)..(131)
<220> FEATURE:
<221> NAME/KEY: O-LINKED
<222> LOCATION: (133)..(133)
<220> FEATURE:
<221> NAME/KEY: O-LINKED
<222> LOCATION: (134)..(134)
<220> FEATURE:
<221> NAME/KEY: O-LINKED
<222> LOCATION: (135)..(135)
<220> FEATURE:
<221> NAME/KEY: O-LINKED
<222> LOCATION: (136)..(136)
<220> FEATURE:
<221> NAME/KEY: O-LINKED
<222> LOCATION: (138)..(138)
<220> FEATURE:
<221> NAME/KEY: O-LINKED
<222> LOCATION: (140)..(140)
<220> FEATURE:
<221> NAME/KEY: O-LINKED
<222> LOCATION: (141)..(141)
<220> FEATURE:
<221> NAME/KEY: O-LINKED-GLYCOSAMINOGLYCAN
<222> LOCATION: (142)..(142)
<220> FEATURE:
<221> NAME/KEY: O-LINKED
<222> LOCATION: (144)..(144)
<220> FEATURE:
<221> NAME/KEY: O-LINKED
<222> LOCATION: (145)..(145)
<220> FEATURE:
<221> NAME/KEY: N-LINKED-GLCNAC
<222> LOCATION: (146)..(146)
<220> FEATURE:
<221> NAME/KEY: O-LINKED
<222> LOCATION: (148)..(148)
<220> FEATURE:
<221> NAME/KEY: O-LINKED
<222> LOCATION: (150)..(150)
```

```
<220> FEATURE:
<221> NAME/KEY: O-LINKED
<222> LOCATION: (152)..(152)
<220> FEATURE:
<221> NAME/KEY: O-LINKED
<222> LOCATION: (153)..(153)
<220> FEATURE:
<221> NAME/KEY: O-LINKED
<222> LOCATION: (159)..(159)

<400> SEQUENCE: 6

Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
        35                  40                  45

Ser Leu Pro Leu Val Thr Thr Pro Ala Pro Glu Thr Cys Glu Gly Arg
    50                  55                  60

Asn Ser Cys Val Ser Cys Phe Asn Val Ser Val Asn Thr Thr Cys
65                  70                  75                  80

Phe Trp Ile Glu Cys Lys Asp Glu Ser Tyr Cys Ser His Asn Ser Thr
                85                  90                  95

Val Ser Asp Cys Gln Val Gly Asn Thr Thr Asp Phe Cys Ser Val Ser
            100                 105                 110

Thr Ala Thr Pro Val Pro Thr Ala Asn Ser Thr Ala Lys Pro Thr Val
        115                 120                 125

Gln Pro Ser Pro Ser Thr Thr Ser Lys Thr Val Thr Ser Gly Thr
    130                 135                 140

Thr Asn Asn Thr Val Thr Pro Thr Ser Gln Pro Val Arg Lys Ser Thr
145                 150                 155                 160

Phe Asp Ala Ala Ser Phe Ile Gly Gly Ile Val Leu Val Leu Glu Ile
                165                 170                 175

Arg Cys His Thr Arg Asn Tyr Ile Pro Asp Leu Lys Lys
            180                 185

<210> SEQ ID NO 7
<211> LENGTH: 197
<212> TYPE: PRT
<213> ORGANISM: homo sapiens
<220> FEATURE:
<221> NAME/KEY: misc_feature
<222> LOCATION: (174)..(174)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid
<220> FEATURE:
<221> NAME/KEY: misc_feature
<222> LOCATION: (189)..(189)
<223> OTHER INFORMATION: Xaa can be any naturally occurring amino acid

<400> SEQUENCE: 7

Met Ser Arg Leu Ser Arg Ser Leu Leu Trp Ala Ala Thr Cys Leu Gly
1               5                   10                  15

Val Leu Cys Val Leu Ser Ala Asp Lys Asn Thr Thr Gln His Pro Asn
            20                  25                  30

Val Thr Thr Leu Ala Pro Ile Ser Asn Val Thr Ser Ala Pro Val Thr
        35                  40                  45
```

```
Ser Leu Pro Leu Val Thr Thr Pro Ala Pro Glu Thr Cys Glu Gly Arg
    50                  55                  60
Asn Ser Cys Val Ser Cys Phe Asn Val Ser Val Val Asn Thr Thr Cys
65                  70                  75                  80
Phe Trp Ile Glu Cys Lys Asp Glu Ser Tyr Cys Ser His Asn Ser Thr
                85                  90                  95
Val Ser Asp Cys Gln Val Gly Asn Thr Thr Asp Phe Cys Ser Val Ser
               100                 105                 110
Thr Ala Thr Pro Val Pro Thr Ala Asn Ser Thr Ala Lys Pro Thr Val
               115                 120                 125
Gln Pro Ser Pro Ser Thr Thr Ser Lys Thr Val Thr Thr Ser Gly Thr
   130                 135                 140
Thr Asn Asn Thr Val Thr Pro Thr Ser Gln Pro Val Arg Lys Ser Thr
145                 150                 155                 160
Phe Asp Ala Ala Ser Phe Ile Gly Gly Ile Val Leu Val Xaa Gly Val
                165                 170                 175
Xaa Ala Val Ile Phe Phe Leu Tyr Lys Xaa Cys Lys Xaa Lys Glu Arg
               180                 185                 190
Asn Tyr His Thr Leu
            195
```

```
<210> SEQ ID NO 8
<211> LENGTH: 195
<212> TYPE: PRT
<213> ORGANISM: homo sapiens

<400> SEQUENCE: 8

Met Ser Arg Leu Ser Arg Ser Leu Leu Trp Ala Ala Thr Cys Leu Gly
1               5                   10                  15
Val Leu Cys Val Leu Ser Ala Asp Lys Asn Thr Thr Gln His Pro Asn
                20                  25                  30
Val Thr Thr Leu Ala Pro Ile Ser Asn Val Lys Ser Leu Ile Ser Cys
            35                  40                  45
Ile Ser Pro Pro Asn Ser Pro Glu Thr Cys Glu Gly Arg Asn Ser Cys
    50                  55                  60
Val Ser Cys Phe Asn Val Ser Val Val Asn Thr Thr Cys Phe Trp Ile
65                  70                  75                  80
Glu Cys Pro Pro Thr Asp Glu Ser Tyr Cys Ser His Asn Ser Thr Val
                85                  90                  95
Ser Asp Cys Gln Val Gly Asn Thr Thr Asp Phe Cys Ser Gly Lys Tyr
               100                 105                 110
Ser Tyr Trp Leu Leu Gly Ser Ile Pro Ala Lys Pro Thr Val Gln Pro
           115                 120                 125
Ser Pro Ser Thr Thr Ser Lys Thr Val Thr Thr Ser Gly Thr Thr Asn
    130                 135                 140
Asn Thr Val Thr Pro Thr Ser Gln Pro Val Arg Lys Ser Thr Phe Asp
145                 150                 155                 160
Ala Ala Ser Phe Ile Gly Gly Ile Val Leu Val Leu Gly Val Gln Ala
                165                 170                 175
Val Ile Phe Phe Leu Tyr Lys Phe Cys Lys Ser Lys Glu Arg Asn Tyr
               180                 185                 190
His Thr Leu
    195
```

```
<210> SEQ ID NO 9
```

```
<211> LENGTH: 13
<212> TYPE: PRT
<213> ORGANISM: Artificial sequence
<220> FEATURE:
<223> OTHER INFORMATION: amino acid linker sequence

<400> SEQUENCE: 9

Glu Phe Gly Ala Gly Leu Val Leu Gly Gly Gln Phe Met
1               5                   10
```

USE OF SOLUBLE CD164 IN INFLAMMATORY AND/OR AUTOIMMUNE DISORDERS

CROSS-REFERENCE TO RELATED APPLICATIONS

This application is a continuation of U.S. application Ser. No. 10/565,741, filed Jan. 23, 2006, now abandoned, which is the U.S. national stage application of International Patent Application No. PCT/EP2004/051596, filed Jul. 23, 2004, the disclosures of which are hereby incorporated by reference in their entirety, including all figures, tables and amino acid or nucleic acid sequences.

FIELD OF THE INVENTION

The present invention relates to the field of inflammation and autoimmune disorders, in particular the discovery of novel proteins useful for preventing and/or treating inflammatory and/or autoimmune disorders.

BACKGROUND OF THE INVENTION

The following discussion is intended to facilitate the understanding of the invention, but is not intended nor admitted to be prior art to the invention.

CD164 is a member of the mucin-like receptor or sialomucin superfamily of glycoproteins. Sialomucins are transmembrane glycoproteins ranging from 50-3000 kD exhibiting limited similarity at the cDNA and amino acid levels. Mucin-like expressed proteins share the common characteristic of bearing numerous O-glycosylations linked to serine and threonine residues, which infer multiple kinds of cell-cell or cell-extracellular matrix interactions. The dense array of O-linked side chains are characterized by an extended structure that makes many of the mucin-like molecules long enough to protrude beyond the polysaccharide glycocalyx that surrounds the cell and also by the optimal exposure and high multiplicity of the terminal sugars. By virtue of the structural configuration as well as negative charge, mucin-like glycoproteins may act as a repulsive barrier unless cells bear specific receptors for mucin (adhesion). Functions of mucin receptors depend on cell types and states of activation correlated with the core mucin peptide and with the cell-specific expression of glycosyl transferases, which in turn regulate the structure and presentation of the O-linked oligosaccharide sidechains, membrane anchorage, signal transduction abilities and or/the trafficking of the mucin to the correct cellular domain.

Human CD164 is an ortholog of murine MGC-24v (*M. musculus*) and rat endolyn (*R. norvegicus*), a membrane protein found in lysosomal and endosomal compartment of mammalian cells. The relationships amongst different isoforms, together with functionally important domains and subcellular distribution of CD164/endolyn, have been described (Chan Y H et al., J. Biol. Chem., 276: 2139-2152, 2001).

In its native state, human CD164 is a disulphide-linked homodimer of two 80-85 kDa subunits. CD164 is highly glycosylated, containing both O- and N-linked glycans. The extracellular region is comprised of two mucin domains (I and II) linked by a non-mucin domain containing intra-disulphide bridges as well as a cysteine-rich motif that resembles a consensus pattern previously found in growth factor and cytokine receptors. CD164 also contains a single-pass trans-membrane domain and a 13-amino acid intracellular region that include a C-terminal motif (i.e. YHTL) able to target the protein to endosomes and lysosomes.

Four human CD164 mRNA species have been described arising by alternative splicing of six bona fide exons from a single genomic transcription unit located on human chromosome 6q21 (Zannettino A, J Biol Regul Homeost Agents, 15: 394-396, 2001; Watt and Chan, Leuk Lymph, 37(: 1-25. 2000). There are probably 4 alternative promoters, two non-overlapping alternative last exons and one internal intron which is not always spliced out. The predominant CD164 (E1-6) isoform represents a 178 amino acid type I transmembrane glycoprotein. The other described isoforms are a sialomucin CD164 or CD164 isoform delta 5 containing 178 amino acids; a 184 residues CD164 isoform delta 4; and a 200 kD principally soluble isoform termed MGC-24 (for Multi-Glycosylated Core protein of 24 kD) lacking the transmembrane anchoring motif and having 189 residues. All isoforms are highly glycosylated proteins with O- and N-linked glycosylation sites (FIG. 1).

CD164 functions include mediating, or regulating, haematopoietic progenitor cell adhesion and the negative regulation of their growth and/or differentiation. CD164 is usually expressed by CD34+ and CD34 lo/– haematopoietic stem cells and associated microenvironmental cells (Watt et al., Blood, 92: 849-866, 1998). CD164 is also expressed by committed myeloid and erythroid colony forming cells, on bone marrow stromal and endothelial cells, weakly on lymphocytes, and on mesenchymal stem cells. CD164 may play a key role in haematopoisesis by facilitating the adhesion of human CD34+ cells to bone marrow stroma and by suppressing CD34+CD38 lo/– haematopoietic progenitor cell proliferation, acting as a potent signaling molecule (Zannettino et al. Blood, 92: 2613-2628, 1998).

These effects involve the CD164 class I and/or II epitopes recognized by the monoclonal antibodies (mAbs) 105A5 and 103B2/9E10. The epitopes are carbohydrate-dependent and are located on the N-terminal mucin domain I (Watt et al., Blood, 95, 3113-3124, 2000; Doyonnas et al., J Immunol, 165: 840-851, 2000). The interaction of haemotopoietic cells with stromal/endothelial cells in their immediate microenvironment is thought to be of major importance in the regulation of haematopoietic stem self-renewal, quiescence, commitment and migration. These interactions involve cooperation between adhesion receptors, their cognate ligands and cytokines. A range of cell adhesion molecules (CAMS) including the Ig, integrin, cadherin, selectin and mucin-like protein families, participate in these processes.

In vitro, CD164 showed a role in myogenic differentiation (Lee et al., Mol Cell Biol, 21: 7696-7706, 2001). Overexpression of CD164 in myoblast cell lines accelerated expression of biochemical markers of differentiation and enhanced formation of multinucleate myotubes, whereas antisense CD164 or soluble extracellular regions of CD164 inhibited myogenesis.

The peanut agglutinin (PNA)-binding site of soluble MGC-24 represents a tumor associated carbohydrate marker expressed in many carcinomas. Total MGC-24 mRNA was found to be lower in human colorectal carcinomas as compared with normal adjacent mucosal tissues (Matsui et al., J Biochem, 127: 1103-1107, 2000). Lymphatic vessel invasion by the carcinoma was correlated to low levels of MGC-24 mRNA in colon carcinomas, whereas high levels did correlate with less venous invasion and less remote metastasis. Monoclonal antibodies specific for CD164 could prove useful for cancer diagnosis or therapy and haematopoiesis inhibition (EP889054, EP761814).

Other CD164-like proteins have been disclosed (NOV25, WO 02/098917; SEQ ID NO: 7852, EP1033401; FIG. 1), but their biological properties have not been analyzed.

SUMMARY OF THE INVENTION

It has been surprisingly found that a soluble protein comprising the mature form of the extracellular domain of human CD164, has an inhibitory effect on the expression of cytokines (namely interferon-γ, IL-2, IL-4, IL-5, IL-10 and TNF-α) in cells that normally produce cytokines when they are stimulated with agents such as concavalin A. Moreover, this soluble fragment of CD164 inhibits relevant physiological responses (such as lymphocytes or macrophages migration) in animal models relevant for inflammatory and/or autoimmune diseases.

Therefore, soluble proteins comprising a sequence having at least 85% of homology with the mature form of the extracellular domain of human CD164 can be used for the manufacture of a medicament for the treatment and/or prevention of inflammatory and/or autoimmune disorders. Pharmaceutical compositions comprising any of these soluble proteins are suitable for treatment and/or prevention of inflammatory and/or autoimmune disorders, and in general can be administered to an individual for inhibiting the expression of cytokines.

Other features and advantages of the invention will become evident from the following detailed description.

DESCRIPTION OF THE FIGURES

FIG. 1: (A) amino acid alignment of full length, human CD164 (hCD164; NCBI Ace. No. NP_006007; SEQ ID NO: 3), human CD164-delta4 (hCD164-DELTA4; NCBI Acc. No. AAG53908; SEQ ID NO: 4), CD164-delta5 (hCD164-DELTA5; NCBI Acc. No. AAG53907; SEQ ID NO: 5), and MGC-24 (hMGC-24; NCBI Acc. No. Q04900; SEQ ID NO: 6). Signal sequences are boxed. The end of the extracellular region is indicated by an arrow. The glycosylation sites are indicated by an asterisk. (B) amino acid alignment of the mature form of the extracellular domains of CD164 (amino acids 1-140 of SEQ ID NO: 1, corresponding to amino acids 24-163 of SEQ ID NO: 3 and to amino acids 1-140 of SEQ ID NO: 2), MGC-24 (amino acids 24-163 of SEQ ID NO: 6), CD164-delta4 (amino acids 24-150 of SEQ ID NO: 4), CD164-delta5 (amino acids 24-145 of SEQ ID NO: 5), SEQ ID NO: 7852 (EP1033401; amino acids 24-163 of SEQ ID NO: 7), and NOV25 (WO 02/098917; amino acids 24-161 of SEQ ID NO: 8). The positions in NOV25 different from SEQ ID NO: 1 are underlined.

FIG. 2: effect of sf-CD164 administration to ConA-stimulated, human PBMC cells-mixture on the expression of IL-2 (A) and TNF-α (B). The X-axis represents the sf-CD164 concentration in µg/ml. The Y-axis represents the percentage of cytokine released by secretion.

FIG. 3: effect of sf-CD164 administration to ConA-stimulated, human CD4 T cells on the expression of IL-2 (A) and TNF-α (B). The X-axis represents the sf-CD164 concentration in µg/ml. The Y-axis represents the percentage of cytokine release by secretion.

FIG. 5: effect of sf-CD164 administration on the cell migration in the animal model for the Thioglycolate- (A) or LPS-induced (B) cell recruitment in the peritoneum. The Y-axis represents the concentration of cells per µl (macrophages in A, activated lymphocytes in B). The asterisks indicate the statistical significance.

DETAILED DESCRIPTION OF THE INVENTION

Figure 4:
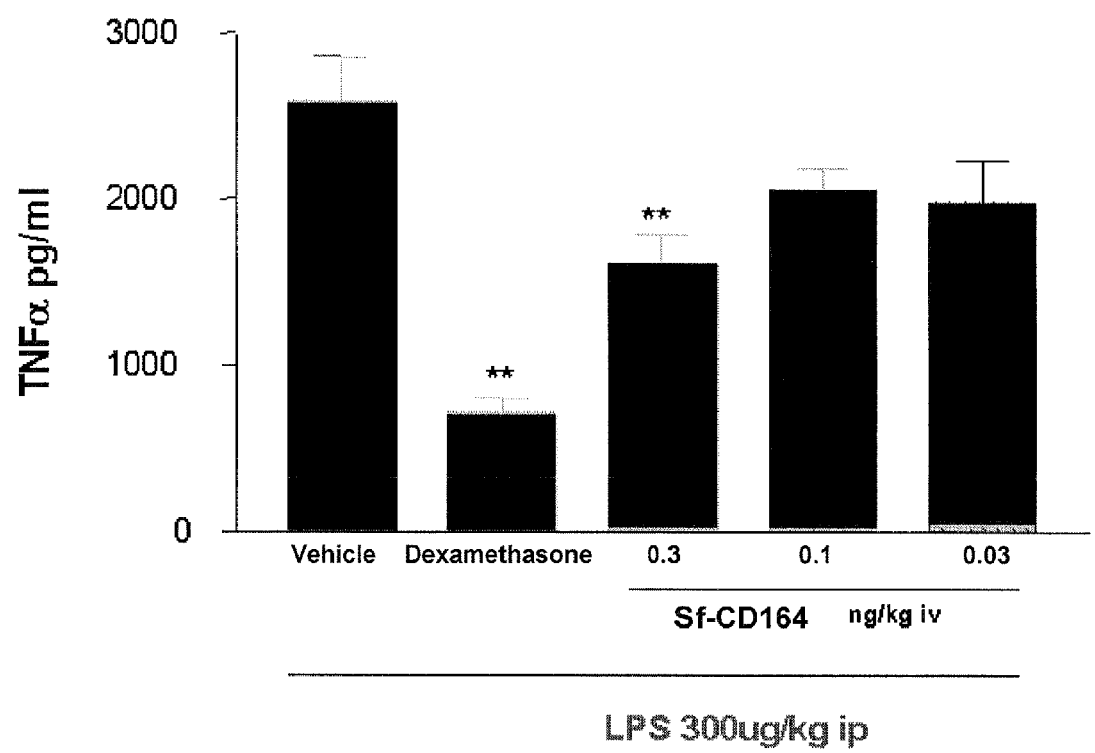
FIG. 4: effect of sf-CD164 administration on TNF-α release in the animal model for LPS-induced, TNF-α release. The asterisks indicate the statistical significance.

In accordance with the present invention, it has been found that the mature form of the extracellular domain of human CD164 (SEQ ID NO: 1) has an inhibitory effect on cellular expression of various cytokines (namely interferon-γ, IL-2, IL-4, IL-5, IL-10 and TNF-α) following the stimulation of these cells with agents such as concanavalin A (ConA). Further confirmations of the therapeutic utility of this protein sequence were obtained in animal models for diseases, wherein the soluble protein demonstrated valuable biological properties in vivo such as the reduction of lymphocyte migration or the inhibition of MBP-(Myelin Basic Protein) specific T cells proliferation.

There is no indication in the prior art that the extracellular domain of human CD164, when isolated from the rest of the molecule as a soluble protein, has any effect on the expression of cytokines or on any other phenomena related to autoimmune and/or inflammatory diseases.

The main object of the present invention is the use of a soluble protein comprising a sequence having at least 85% of homology with the mature form of the extracellular domain of human CD164 (SEQ ID NO: 1) for the manufacture of a medicament for treatment and/or prevention of inflammatory or/and autoimmune disorders.

Amongst the soluble proteins that can be used accordingly to the present invention, the most preferred soluble proteins are the mature form of the extracellular domain of human CD164 (SEQ ID NO: 1), or this latter sequence fused to the signal sequence of human CD 164.

Other preferred soluble proteins that can be used accordingly to the present invention, are variants of SEQ ID NO: 1 in the form of active muteins or isoforms of SEQ ID NO: 1.

Isoforms of human CD164 having at least 85% of homology with the mature form of the extracellular domain of human CD164 (SEQ ID NO: 1) are known in the literature (Chan Y H et al., J Biol Chem, 276: 2139-2152, 2001; FIG. 1). One of them called MGC-24 (SEQ ID NO: 6) is known to be soluble since it lacks a functional transmembrane domain, while two others called CD164-delta 4 (SEQ ID NO: 4) and CD164-delta 5 (SEQ ID NO: 5) still conserve a transmembrane domain. Therefore, the mature form of the extracellular domain of these latter membrane-bound isoforms can be considered useful according to this invention.

As "soluble proteins", the present invention intends protein sequences not containing any sequences allowing the integration in a cellular membrane, such as the transmembrane domain in human full length CD164. These soluble proteins, when expressed by cells, are therefore expected to be localized in the cells or, preferably, secreted in the extracellular space if fused to a signal sequence.

Soluble proteins comprising a sequence having at least 85% of homology with the mature form of the extracellular domain of human CD164 (SEQ ID NO: 1) are known in the literature (Lee Y N et al., Mol Cell Biol, 21: 7696-7706, 2001) but there is no indication of any utility for the treatment and/or prevention of inflammatory and/or autoimmune disorders.

The soluble protein sequences defined in the present invention as being useful for the treatment and/or prevention of inflammatory and/or autoimmune disorders are also clearly distinct from any other human sequence having, or supposed to have, similar properties.

WO 02/098917 discloses the protein NOV25 (SEQ ID NO: 8; FIG. 1B) comprising a sequence homologous at 80% with the mature form of the extracellular domain of human CD164 (SEQ ID NO: 1), and suggests that it can be useful in a variety of diseases, including autoimmune disease. However, this use is merely speculative, and moreover the document fails to recognize the therapeutic utility of the soluble fragment that can be isolated from the potential extracellular domain of this protein, that is predicted to be localized on a cellular membrane.

EP1033401 discloses a protein (SEQ ID NO: 7582) comprising a sequence identical to the mature form of the extracellular domain of human CD164 (SEQ ID NO: 7; FIG. 1B). Even though it is suggested therein a hypothetical therapeutic use of this protein in medicine for any sorts of disease, this document also fails to recognize the therapeutic utility of the soluble fragment that can be isolated from the potential extracellular domain of this protein.

As "active", the present invention defines any variant of the mature form of the extracellular domain of human CD164 (SEQ ID NO: 1) having at least 85% of homology with this sequence that, according to any of the assay presented in the examples, has a comparable, or even increased, activity when compared to SEQ ID NO: 1, and should be as well accepted for any of the claimed uses and methods.

By the activity being "comparable" is meant that the activity measured in any of the described assays for the variant of the soluble protein is at least of the same order of magnitude, and preferably 75%, 80%, 85%, 90%, 95%, 96%, 97%, 98%, 99%, or 100%, and not more than 101%, 102%, 103%, 104%, 105%, 110%, 115%, 120% or 125% of the activity measured using a soluble protein as defined by SEQ ID NO: 1.

By the activity being "increased" is meant that the activity measured in any of the described assays for the variant of the soluble protein is at least 125%, 130%, 135%, 140%, 145%, 150%, 155%, 160%, 170%, 180%, 190%, 200%, 225%, 250%, 275%, 300%, 325%, 350%, 375%, 400%, 450%, or 500% of the activity measured using a soluble protein as defined by SEQ ID NO: 1.

As used herein the term "muteins" refers to any sequence having at least 85% of homology with the mature form of the extracellular domain of human CD164 (SEQ ID NO: 1) that can be generated by inserting, deleting, and/or substituting one or more amino acid residues in SEQ ID NO: 1. Similar active muteins can be natural, as the ones corresponding to an orthologous protein (i.e. encoded by a non-human gene that has evolved from the common ancestor for CD164) or from polymorphisms in human genome. In cases where the nucleotide substitutions result in one or more amino acid changes, preferred soluble proteins include those that retain one or more anti-inflammatory- or/and anti-autoimmune-related activity.

Alternatively, these sequences are synthetic or artificial, which can be prepared by known chemical synthesis, recombinant DNA technology, site-directed mutagenesis, or any other known technique suitable thereof, which provide a finite set of substantially corresponding mutated or shortened peptides or polypeptides which can be routinely obtained and tested by one of ordinary skill in the art using the teachings presented in the prior art and in the Examples of the present invention.

Preferred changes in these active muteins are commonly known as "conservative" or "safe" substitutions. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provide many models on which the selection of conservative amino acids substitutions can be performed on the basis of statistical and physico-chemical studies on the sequence and/or the structure of natural protein (Rogov S I and Nekrasov A N, Protein Eng, 14: 459-463, 2001). Protein design experiments have shown that the use of specific subsets of amino acids can produce foldable and active proteins, helping in the classification of amino acid "synonymous" substitutions that can be more easily accommodated in protein structure (Murphy L R et al., Protein Eng, 13: 149-52, 2000). The synonymous amino acid groups and more preferred synonymous groups are those defined in Table I.

Alternatively, amino acids in the soluble proteins of the invention that are essential for function can also be identified by methods known in the art, such as site-directed mutagenesis or alanine-scanning mutagenesis (see, e.g., Cunningham, et al., Science, 244: 1081-5, 1989). Of special interest are substitutions of charged amino acids with other charged or neutral amino acids that may produce proteins with highly desirable improved characteristics, such as less aggregation. Aggregation may not only reduce activity but also be problematic when preparing pharmaceutical or physiologically acceptable formulations, because aggregates can be immunogenic (Cleland et al., Crit. Rev Ther Drug Carrier Syst, 10: 307-77, 1993).

Other examples of production of amino acid substitutions in proteins which can be used for obtaining muteins of soluble proteins for the uses of the present invention include any known method steps, such as presented in U.S. Pat. Nos. 4,959,314, 4,588,585, 4,737,462, 5,116,943, 4,965,195; 4,879,111, 5,017,691, and 4,904,584.

Alternatively, the active mutein may result from sequence alterations reducing the immunogenicity of said soluble protein when administered to a mammal. The literature provides many example on these sequence alterations that can be designed and introduced at this scope or for other functional optimizations that allow a safe and effective administration of a therapeutic protein, especially when it is non-human, non-mammalian, or non-natural protein (Vasserot A P et al., Drug Disc Today, 8: 18-126, 2003; Marshall S A et al., Drug Disc Today, 8: 212-221, 2003; Schellekens H, Nat Rev Drug Disc, 1: 457-462, 2002; Gendel S M, Ann NY Acad SCI, 964: 87-98, 2002; Graddis T J et al., Curr Pharm Biotechnol, 3: 285-97, 2002; WO 03/104263; WO 03/006047; WO 02/98454, WO 02/96454; WO 02/79415; WO 02/79232; WO 02/66514; WO 01/40281; WO 98/52976; WO 96/40792; WO 94/11028).

It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteines or prolines. These alterations may occur at the amino or carboxy termini or anywhere between those terminal positions, interspersed either individually among residues in the sequence or in one or more contiguous groups within the sequence.

As a practical matter, whether any particular polypeptide is a percentage homologous to the mature form of the extracellular domain of human CD164 (SEQ ID NO: 1) can be determined conventionally using known computer programs. Such algorithms and programs include, but are by no means limited to, TBLASTN, BLASTP, FASTA, TFASTA, and CLUSTALW (Pearson and Lipman, (1988) Proc Natl Acad Sci USA 85(8):2444-8; Altschul et al., (1990) J Mol Biol 215(3):403-410; Thompson et al., (1994) Nucleic Acids Res 22(2):4673-4680; Higgins et al., (1996) Meth Enzymol 266: 383-402; Altschul et al., (1997) Nuc Acids Res 25: 3389-3402; Altschul et al., (1993) Nature Genetics 3: 266-272). In a particularly preferred embodiment, protein and nucleic acid sequence homologies are evaluated using the Basic Local Alignment Search Tool ("BLAST"), which is well known in the art (See, e.g., Karlin and Altschul (1990) Proc Natl Acad Sci USA 87(6):2264-8; Altschul et al., 1990, 1993, 1997, all supra).

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (i.e., aligned) by means of a scoring matrix, many of which are known in the art. Preferably, the scoring matrix used is the BLOSUM62 matrix (see, Gonnet et al., (1992) Science 256 (5062):1443-5; Henikoff and Henikoff (1993) Proteins 17(1): 49-61). Less preferably, the PAM or PAM250 matrices may also be used (See, e.g., Schwartz and Dayhoff, eds, (1978) Matrices for Detecting Distance Relationships: Atlas of Protein Sequence and Structure, Washington: National Biomedical Research Foundation). The BLAST programs evaluate the statistical significance of all high-scoring segment pairs identified, and preferably selects those segments which satisfy a user-specified threshold of significance, such as a user-specified percent homology. Preferably, the statistical significance of a high-scoring segment pair is evaluated using the statistical significance formula of Karlin (See, e.g., Karlin and Altschul, (1990) Proc Natl Acad Sci USA 87(6):2264-8). The BLAST programs may be used with the default parameters or with modified parameters provided by the user. Preferably, the parameters are default parameters.

A preferred method for determining the best overall match between a query sequence (a sequence of the present invention) and a subject sequence, also referred to as a global sequence alignment, can be determined using the FASTDB computer program based on the algorithm of Brutlag et al. (1990) Comp. App. Biosci. 6: 237-245. In a sequence alignment the query and subject sequences are both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group=25 Length=0, Cutoff Score=1, Window Size=sequence length, Gap Penalty=5, Gap Size Penalty=0.05, Window Size=247 or the length of the subject amino acid sequence, whichever is shorter.

If the subject sequence is shorter than the query sequence due to N- or C-terminal deletions, not because of internal deletions, the results, in percent identity, must be manually corrected because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, that are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query amino acid residues outside the farthest N- and C-terminal residues of the subject sequence.

For example, a 90 amino acid residue subject sequence is aligned with a 100-residue query sequence to determine percent identity. The deletion occurs at the N-terminus of the subject sequence and therefore, the FASTDB alignment does not match/align with the first residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%.

In preferred embodiments, the post-translationally modified forms of soluble proteins comprising a sequence having at least 85% of homology with the mature form of the extracellular domain of human CD164 (SEQ ID NO: 1) can be used for the manufacture of a medicament for treatment and/or prevention of inflammatory or/and autoimmune disorders. In particular, these proteins can be acetylation, amidation, glycosylated, phosphorylated, and/or myristoylated.

Human CD164 is known to be modified with such groups and a series of specific positions can be indicated as set forth in SEQ ID NO: 1:
 a) Potential N-glycosylation sites are located at residues 3, 9, 18, 49, 54, 71, 81, 98 and 123;
 b) Potential O-glycosylated sites are located at residues 11, 12, 17, 20, 21, 25, 26, 31, 32, 89, 90, 92, 96, 99, 100, 104, 108, 110, 111, 112, 113, 115, 117, 118, 119, 121, 122, 125, 127, 129, 130, 136.
 c) Potential cAMP- and cGMP-dependent protein kinase phosphorylation sites are located at residues 134 to 137;
 d) Potential Protein Kinase C phosphorylation sites are located at residues 100 to 102 and 112 to 114;
 e) Potential Casein kinase II phosphorylation sites are located at residues 73 to 76 and 136 to 139;
 f) Potential N-myristoylation site in sf-CD164 is located at residue 119.

It is evident that such modifications can be also present in the corresponding positions of the homologous soluble proteins defined above as identified by sequence alignment (FIG. 1).

In a further preferred embodiment, the soluble protein comprising a sequence having at least 85% of homology with the mature form of the extracellular domain of human CD164 (SEQ ID NO: 1) is a soluble fusion protein.

These soluble fusion proteins can be obtained by cloning a polynucleotide encoding soluble protein comprising a sequence having at least 85% of homology with the mature form of the extracellular domain of human CD164 (SEQ ID NO: 1) in frame to the coding sequences for a heterologous protein sequence.

The term "heterologous", when used herein, is intended to designate any polypeptide other than a human CD164 polypeptide.

Example of heterologous sequences, that can be comprised in the soluble fusion proteins either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography.

Many of these heterologous sequences are commercially available in expression plasmids since these sequences are commonly included in the fusion proteins in order to provide additional properties without significantly impairing the specific biological activity of the protein fused to them (Terpe K, Appl Microbiol Biotechnol, 60: 523-33, 2003). Examples of such additional properties are a longer lasting half-life in body fluids, the extracellular localization, or an easier purification procedure as allowed by the a stretch of Histidines forming the so-called "histidine tag" (Gentz et al., Proc Natl Acad Sci USA, 86: 821-4, 1989) or by the "HA" tag, an epitope derived from the influenza hemagglutinin protein (Wilson et al., Cell, 37: 767-78, 1994). If needed, the heterologous sequence can be eliminated by a proteolytic cleavage, for example by inserting a proteolytic cleavage site between the soluble protein and the heterologous sequence, and exposing the purified soluble fusion protein to the appropriate protease. These features are of particular importance for the soluble fusion proteins since they facilitate their production and use in the preparation of pharmaceutical compositions. For example, the soluble protein used in the examples (sf-CD164; SEQ ID NO: 2) was purified by means of a hexa-histidine peptide fused at the C-terminus of the soluble CD164. When the soluble fusion protein comprises an immunoglobulin region, the fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met (SEQ ID NO: 9) introduced between the sequence of the substances of the invention and the immunoglobulin sequence. The resulting fusion protein has improved properties, such as an extended residence time in body fluids (half-life), increased specific activity, increased expression level, or the purification of the fusion protein is facilitated.

In a preferred embodiment, the soluble protein is fused to the constant region of an Ig molecule. Preferably, it is fused to heavy chain regions, like the CH2 and CH3 domains of human IgG1, for example. Other isoforms of 1 g molecules are also suitable for the generation of fusion proteins according to the present invention, such as isoforms $IgG_2$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

The soluble proteins and soluble fusion proteins comprising a sequence having at least 85% of homology with the mature form of the extracellular domain of human CD164 (SEQ ID NO: 1) can be extracted and isolated from bodily fluids, cells, or tissues of human or mammalian naturally expressing them naturally. In particular, cells whether directly isolated or cultured, can express these soluble proteins (naturally or following the exposure to an inducing agent) and secrete them. Methods for purifying proteins are known in the art, and include the use of detergents or chaotropic agents to disrupt particles followed by differential extraction and separation of the polypeptides by ion exchange chromatography, affinity chromatography, sedimentation according to density, and gel electrophoresis.

In general, the soluble proteins and soluble fusion proteins can be prepared by any procedure known in the art, including recombinant DNA-related technologies and chemical synthesis technologies.

Recombinant DNA-related technologies allow producing the soluble proteins and soluble fusion proteins by first generating polynucleotides encoding them. These nucleic acids can be obtained by PCR from genomic DNA or, more efficiently, from a vector containing the full sequence of human CD164 (SEQ ID NO: 3) or any other relevant homologous sequences. The oligonucleotide primers complementary to the desired sequence contain restriction endonuclease sequences allowing the digestion by specific restriction endonucleases for further cloning, taking care to ensure that the sequence encoding the soluble protein is positioned properly with respect to the polyA signal and the rest of the other sequences in the expression plasmid.

Using common genetic engineering techniques, these polynucleotides can be cloned in replicable expression vector of viral or plasmid origin which are used to transform a prokaryotic or eukaryotic host cell, using episomal or non-/homologously integrated vectors, as well as transformation-, infection-, precipitation-, or transfection-based technologies. These vectors should allow the expression of the recombinant proteins in the prokaryotic or eukaryotic host cell under the control of their own transcriptional initiation/termination regulatory sequences, which are chosen to be constitutively active or inducible in said cell. A cell line substantially enriched in such cells can be then isolated to provide a stable cell line expressing the protein of interest.

Many books and reviews provides teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001).

A typical expression vector should comprise:
  a) a DNA sequence coding for a soluble protein or a soluble fusion protein comprising a sequence having at least 85% of homology with the mature form of the extracellular domain of human CD164 (SEQ ID NO: 1); and
  b) an expression cassette;
wherein said sequence (a) is operably associated with a tissue-specific or a constitutive promoter included in sequence (b).

The expression vector is any of the mammalian, yeast, insect or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism into which the expression vector is introduced (U.S. Pat. No. 5,082,767; Gustafsson C et al., Trends Biotechnol, 22: 346-53, 2004).

Factors of importance in selecting a particular plasmid or viral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species. A recombinant vector according to the invention comprises, but is not limited to, a YAC (Yeast Artificial Chromosome), a BAC (Bacterial Artificial Chromosome), a phage, a phagemid, a cosmid, a plasmid, or even a linear DNA molecule which may consist of a chromosomal, non-chromosomal, semi-synthetic or synthetic DNA.

Generally, recombinant expression vectors will include origins of replication, selectable markers permitting transformation of the host cell, and a promoter derived from a highly expressed gene to direct transcription of a downstream structural sequence. The heterologous structural sequence is assembled in appropriate phase with translation initiation and termination sequences, and preferably a leader sequence capable of directing secretion of the translated protein into the periplasmic space or the extracellular medium. In a specific embodiment wherein the vector is adapted for transfecting and expressing desired sequences in mammalian host cells, preferred vectors will comprise an origin of replication in the desired host, a suitable promoter and enhancer, and also any necessary ribosome binding sites, polyadenylation sites, splice donor and acceptor sites, transcriptional termination sequences, and 5'-flanking non-transcribed sequences. DNA sequences derived from the SV40 viral genome, for example SV40 origin, early promoter, enhancer, splice and polyadenylation sites may be used to provide the required non-transcribed genetic elements.

The suitable promoter regions used in the expression vectors of the present invention are chosen taking into account the cell host in which the heterologous gene is expressed. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell, such as, for example, a human or a viral promoter. The promoter used may be constitutive or inducible.

A suitable promoter may be heterologous with respect to the nucleic acid for which it controls the expression or alternatively can be endogenous to the native polynucleotide containing the coding sequence to be expressed. Additionally, the promoter is generally heterologous with respect to the recombinant vector sequences within which the construct promoter/coding sequence has been inserted.

Promoter regions can be selected from any desired gene using, for example, CAT (chloramphenicol transferase) vectors and more preferably pKK232-8 and pCM7 vectors. Preferred bacterial promoters are the LacI, LacZ, the T3 or T7 bacteriophage RNA polymerase promoters, the gpt, lambda PR, PL and trp promoters (EP 0036776), the polyhedrin promoter, or the p10 protein promoter from baculovirus (Kit Novagen) (Smith et al., (1983) Mol Cell Biol 3(12):2156-65; O'Reilly et al., 1992), the lambda PR promoter or also the trc promoter. Eukaryotic promoters include CMV immediate early, HSV thymidine kinase, early and late SV40, LTRs from retrovirus, and mouse metallothionein-L. In addition, promoters specific for a particular cell type may be chosen, such as those facilitating expression in adipose tissue, muscle tissue, or liver. Selection of a convenient vector and promoter is well within the level of ordinary skill in the art.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

The vectors may also contain additional, non-coding sequences, including for example, but not limited to non-coding 5' and 3' sequences, vector sequence, sequences used for purification, probing, or priming. For example, heterologous sequences include transcribed, non-translated sequences that may play a role in transcription, and mRNA processing, for example, ribosome binding and stability of mRNA.

Selectable markers confer an identifiable change to the cell permitting easy identification of cells containing the expression construct. The selectable marker genes for selection of transformed host cells are preferably dihydrofolate reductase or neomycin resistance for eukaryotic cell culture, TRP1 for S. cerevisiae or tetracycline, rifampicin or ampicillin resistance in E. coli, or levan saccharase for mycobacteria, this latter marker being a negative selection marker.

As a representative but non-limiting example, useful expression vectors for bacterial use can comprise a selectable marker and a bacterial origin of replication derived from commercially available plasmids comprising genetic elements of pBR322 (ATCC 37017). Such commercial vectors include, but are not limited to, pKK223-3 (Pharmacia, Uppsala, Sweden) and pGEM1 (Promega Biotec, Madison, Wis., USA).

Large numbers of other suitable vectors are known to those of skill in the art, and are commercially available, such as the following bacterial vectors: pTrc-His, pET30-His, pQE70, pQE60, pQE-9 (Qiagen), pbs, pD10, phagescript, psiX174, pbluescript SK, pbsks, pNH8A, pNH16A, pNH18A, pNH46A (Stratagene); ptrc99a, pKK223-3, pKK233-3, pDR540, pRIT5 (Pharmacia); pWLNEO, pSV2CAT, pOG44, pXT1, pSG (Stratagene); pSVK3, pBPV, pMSG, pSVL (Pharmacia); pQE-30 (QIAexpress).

A suitable vector for the expression of polypeptides is a baculovirus vector that can be propagated in insect cells and in insect cell lines. A specific suitable host vector system is the pVL1392/1393 baculovirus transfer vector (Pharmingen) that is used to transfect the SF9 cell line (ATCC No. CRL 1711) which is derived from *Spodoptera frugiperda*. Further suitable baculovirus vectors are known to those skilled in the art, for example, FastBacHT. Other suitable vectors for the expression of an APM1 globular head polypeptide in a baculovirus expression system include, but are not limited to, those described by Chai et al. (1993; Biotechnol Appl Biochem. December; 18 (Pt 3): 259-73); Vlasak et al. (1983; Eur J Biochem September 1; 135(1): 123-6); and Lenhard et al. (1996; Gene March 9; 169(2): 187-90).

Further suitable vectors for the expression of polypeptides are mammalian vectors. A number of suitable vector systems are known to those skilled in the art, for example, pcDNA4HisMax, pcDNA3.1 Hygro-His and pcDNA3.1 Hygro.

Further suitable vectors for the expression of polypeptides are viral vector, such as the ones derived from an adenovirus. Preferred adenovirus vectors according to the invention are those described by Feldman and Steg (1996; Semin Interv Cardiol 1(3):203-8) or Ohno et al. (1994; Science 265(5173): 781-4).

Retrovirus vectors and adeno-associated virus vectors are generally understood to be the recombinant gene delivery systems of choice for the transfer of exogenous polynucleotides in vivo, particularly to mammals, including humans. These vectors provide efficient delivery of genes into cells, and the transferred nucleic acids are stably integrated into the chromosomal DNA of the host.

Another possibility to express polypeptides is to activate endogenously the genes by introducing regulatory sequence into the right locus of the genome by homologous recombination, thus operably linking the regulatory sequence with the gene, the expression of which is required to be induced (WO 91/09955; WO 02/10372).

Host cells may be either prokaryotic or eukaryotic. Preferred are eukaryotic hosts, e.g. mammalian cells, such as human, monkey, mouse, and Chinese Hamster Ovary (CHO) cells, because they provide post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences in cloned mammalian gene products and secretes peptides bearing leader sequences (i.e., pre-peptides).

Preferred host cells used as recipients for expressing the soluble proteins are the following:
a) Prokaryotic host cells: *Escherichia coli* strains (I.E. DH5-α strain), *Bacillus subtilis*, *Salmonella typhimurium*, and strains from species like *Pseudomonas*, *Streptomyces* and *Staphylococcus*;
b) Eukaryotic host cells: HeLa cells (ATCC No. CCL2; No. CCL2.1; No. CCL2.2), Cv 1 cells (ATCC No. CCL70), COS cells (ATCC No. CRL1650; No. CRL1651), Sf-9 cells (ATCC No. CRL1711), C127 cells (ATCC No. CRL-1804), 3T3 (ATCC No. CRL-6361), CHO (ATCC No. CCL-61), human kidney 293 (ATCC No. 45504; No. CRL-1573), BHK (ECACC No. 84100501; No. 84111301), PLC cells, HepG2, and Hep3B.

For Eukaryotic hosts (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

If the nucleic acid encoding the soluble protein lacks a methionine to serve as the initiation site, an initiating methionine can be introduced next to the first codon of the nucleic acid using conventional techniques. Similarly, if the insert from the soluble CD164 polypeptide cDNA lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

Depending upon the host employed in a recombinant production procedure, the polypeptides of the present invention may be glycosylated or may be non-glycosylated. In addition, the soluble proteins may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

The soluble proteins, given their limited length, can be also produced by chemical synthesis technologies, for example by solid phase synthesis and liquid phase synthesis. As a solid phase synthesis, for example, the amino acid corresponding to the C-terminus of the peptide to be synthetized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner.

Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and C12-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method. Totally synthetic proteins of a length comparable to the one of the proteins of the invention are disclosed in the literature (Brown A et al., J Pept Sci 2: 40-46, 1996; Muir T W, Annu Rev Biochem, 72: 249-89, 2003; Casi G and Hilvert D, Curr Opin Struct Biol, 13: 589-94, 2003).

The chemical synthesis of the soluble proteins allows expanding the natural repertoire of protein structure and function by making use of non-natural amino acids (Anthony-Cahill S J and Magliery T J, Curr Pharm Biotechnol, 3: 285-97, 2002). These molecules can be designed on the sequence and/or the structure of the soluble proteins in order to select the residues can be chemically modified at the level of amino acid side chains, of amino acid chirality, and/or of the peptide backbone, and then to improve relevant properties, such as potency, easiness of purification, half-life. Preferred alternative, "synonymous" groups for amino acids to be included are those defined in Table II. The techniques for the synthesis and the development of these compounds are well known in the art (Hruby V J and Balse P M, Curr Med Chem, 7: 945-70, 2000; Golebiowski A et al., Curr Opin Drug Discov Devel, 4: 428-34, 2001; Villain M et al., Chem Biol, 8: 673-9, 2001, WO 02/10195). Various methodology for incorporating unnatural amino acids into proteins, using both in vitro and in vivo translation systems, to probe and/or improve protein structure and function are also disclosed in the literature (Dougherty D A, Curr Opin Chem Bio, 4: 645-52, 2000).

The purification of synthetic or recombinant soluble proteins that can be used according to the invention, can be carried out by any one of the methods known for this purpose, i.e. any conventional procedure involving precipitation, chromatography (anion or cation exchange chromatography, phosphocellulose chromatography, hydrophobic interaction chromatography, affinity chromatography, hydroxylapatite chromatography and lectin chromatography), electrophoresis, differential extraction, salt fractionation, centrifugation or the like. See, for example, Methods in Enzymology for a variety of methods for purifying proteins.

A purification procedure that may be used in preference is affinity chromatography using monoclonal antibodies, or any other chemical groups that bind the target protein (directly soluble CD164 or, if it is a soluble fusion protein, the heterologous sequence such as an histidine tag) with sufficient affinity and specificity. The binding groups are produced and immobilized on a gel matrix contained within a column. Impure preparations containing the proteins are passed through the column. The soluble protein will be bound to the column by affinity while the impurities will pass through. After washing away remaining impurities, the soluble protein can be eluted from the gel by a change in pH or ionic strength. Alternatively, HPLC (High Performance Liquid Chromatography) can be used. The elution can be carried using a water-acetonitrile-based solvent commonly employed for protein purification.

Alternatively, the soluble proteins can be isolated from milk of transgenic animals expressing the soluble proteins applying any of the large number of methods disclosed in the literature (Protein Purification Applications, A Practical Approach (New Edition), Edited by Simon Roe, AEA Technology Products and Systems, Biosciences, Harwell; Clark (1998) J Mammary Gland Biol Neoplasia 3: 337-50; U.S. Pat. No. 6,140,552).

The soluble protein comprising a sequence having at least 85% of homology with the mature form of the extracellular domain of human CD164 (SEQ ID NO: 1) can be produced, formulated, administered, or generically used for the manufacture of a medicament for treatment and/or prevention of inflammatory or/and autoimmune disorders as an active derivative, a proteolysis-resistant modified form, a conjugate, a complex, a fraction, a precursor, and/or a salt.

The term "derivatives" as herein used refers to derivatives which can be prepared from the functional groups present on the lateral chains of the amino acid moieties or on the N- or C-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The term "fraction" refers to any fragment of the polypeptidic chain of the compound itself, alone or in combination with related molecules or residues bound to it, for example residues of sugars or phosphates, or aggregates of the original polypeptide or peptide. Such molecules can result also from other modifications which do not normally alter primary sequence, for example in vivo or in vitro chemical derivatization of peptides (acetylation or carboxylation), those made by modifying the pattern of phosphorylation (introduction of phosphotyrosine, phosphoserine, or phosphothreonine residues) or glycosylation (by exposing the peptide to enzymes which affect glycosylation e.g., mammalian glycosylating or deglycosylating enzymes) of a peptide during its synthesis and processing or in further processing steps.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The conjugate or complex cane be formed with a molecule chosen amongst radioactive labels, biotin, fluorescent labels, cytotoxic agents, drug delivery agents. These conjugates or complexes can be generated, using molecules and methods known in the art, for example for allowing the detection of the interaction with other proteins (radioactive or fluorescent labels, biotin), for improving therapeutic efficacy (cytotoxic agents), or for improving drug delivery efficacy, using polymers such as polyethylene glycol and other natural or synthetic polymers (Pillai O and Panchagnula R, Curr Opin Chem Biol, 5: 447-451, 2001).

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the polypeptide with consideration of effects on functional or antigenic domains of the polypeptide. There are a number of attachment methods available to those skilled in the art, e.g., EP 0 401 384, herein incorporated by reference (coupling PEG to G-CSF), see also Malik et al. (1992) Exp Hematol 20(8):1028-35, reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

A polypeptide resistant to proteolysis, can be generated by replacing a —CONH— peptide bond with one or more of the following: a (CH2NH) reduced bond; a (NHCO) retro inverso bond; a (CH2-O) methylene-oxy bond; a (CH2-S) thiomethylene bond; a (CH2CH2) carba bond; a (CO—CH2) cetomethylene bond; a (CHOH—CH2) hydroxyethylene bond); a (N—N) bound; a E-alcene bond; or a —CH=CH— bond. Thus, the invention also encompasses a soluble CD164 or a variant thereof in which at least one peptide bond has been modified as described above. In addition, amino acids have chirality within the body of either L or D. In some embodiments it is preferable to alter the chirality of the amino acids in order to extend half-life within the body. Thus, in some embodiments, one or more of the amino acids are preferably in the L configuration. In other embodiments, one or more of the amino acids are preferably in the D configuration.

The therapeutic applications of the polypeptides of the invention and of the related reagents can be evaluated (in terms or safety, pharmacokinetics and efficacy) by the means of the in vivo or in vitro assays making use of animal cell, tissues and models allowing to detect an inhibition of cytokine release and/or expression, as well in vivo or in vitro assays, such as the inhibition of cellular recruitment. Further characterization of the biological and therapeutic activities described in the present invention can be obtained by applying various in molecular biology technologies, such as two-dimensional gel electrophoresis or RNA interference.

One specific embodiment for a method for delivering a soluble protein to the interior of a cell of a vertebrate in vivo comprises the step of introducing a preparation comprising a physiologically acceptable carrier and a naked polynucleotide operatively coding for the polypeptide of interest into the interstitial space of a tissue comprising the cell, whereby the naked polynucleotide is taken up into the interior of the cell and has a physiological effect. This is particularly applicable for transfer in vitro but it may be applied to in vivo as well.

A polynucleotide sequence encoding for a soluble protein comprising a sequence having at least 85% of homology with the mature form of the extracellular domain of human CD164 (SEQ ID NO: 1) can be used for the manufacture of a medicament for treatment and/or prevention of inflammatory or/and autoimmune disorders. These polynucleotides can be also used for the generation of non-human animals and plants that express recombinant CD164 polypeptides. The animals or plants can be transgenic, i.e. each of their cells contains a gene encoding the CD164 polypeptide, or, alternatively, a polynucleotide encoding the polypeptide can be introduced into somatic cells of the animal or plant, e.g. into mammary secretory epithelial cells of a mammal. In preferred embodiments, the non-human animal is a mammal such as a cow, sheep, goat, pig, or rabbit. Methods of making transgenic animals such as mammals are well known to those of skill in the art, and any such method can be used in the present invention. Moreover, transgenic mammals can be generated that secrete the recombinant soluble proteins polypeptides in their milk. Typically, the encoded polypeptide will include a signal sequence to ensure the secretion of the protein into the milk.

Compositions for use in vitro and in vivo comprising a "naked" polynucleotide are described in the prior art (WO 90/11092; WO 95/11307; Tascon et al., Nature Medicine 2: 888-892, 1996). In still another embodiment of the invention, the transfer of a naked polynucleotide into cells may be proceeded with a particle bombardment (biolistic), said particles being DNA-coated microprojectiles accelerated to a high velocity allowing them to pierce cell membranes and enter cells without killing them, such as described by Klein et al. ((1990) Curr Genet February; 17(2):97-103). In a further embodiment, the polynucleotide of the invention may be entrapped in a liposome (Ghosh and Bacchawat, (1991) Targeted Diagn Ther 4: 87-103; Wong et al., (1980) Gene 10: 87-94; Nicolau et al., (1987) Methods Enzymol 149: 157-76). These liposomes may further be targeted to cells expressing LSR by incorporating leptin, triglycerides, ACRP30, or other known LSR ligands into the liposome membrane. The amount of vector to be injected to the desired host organism varies according to the site of injection. As an indicative dose, it will be injected between 0.1 and 100 µg of the vector in an animal body, preferably a mammal body, for example a mouse body. In another embodiment of the vector according to the invention, it may be introduced in vitro in a host cell, preferably in a host cell previously harvested from the animal to be treated and more preferably a somatic cell such as a muscle cell. In a subsequent step, the cell that has been transformed with the vector coding for the desired CD164 polypeptide or the desired fragment thereof is reintroduced into the animal body in order to deliver the recombinant protein within the body either locally or systemically.

For in vivo administration, the polynucleotides can be administered in any suitable formulation, at any of a range of concentrations (e.g. 1-500 µg/ml, preferably 50-100 µg/ml), at any volume (e.g. 1-100 ml, preferably 1 to 20 ml), and can be administered any number of times (e.g. 1, 2, 3, 5, or 10 times), at any frequency (e.g. every 1, 2, 3, 5, 10, or any number of days). Suitable concentrations, frequencies, modes of administration, etc. will depend upon the particular polynucleotide, vector, animal, etc., and can readily be determined by one of skill in the art.

The soluble protein comprising a sequence having at least 85% of homology with the mature form of the extracellular domain of human CD164 (SEQ ID NO: 1)/are capable of inhibiting proinflammatory- and/or immune-related cytokine expression, and are thus believed to prevent and/or treat "inflammatory and/or autoimmune disorders".

The primary function of the immune system is to protect an individual against infection by foreign invaders such as microorganisms, it may happen that the immune system attacks the individual's own tissues, leading to pathologic states known as autoimmune diseases, which are frequently associated with inflammatory processes.

In particular, CD4+ T cells can be assigned to two different subsets called T helper type 1 cells (Th1) and T helper type 2 cells (Th2) on the basis of distinct, non-overlapping cytokine expression patterns. Th1 is characterized by the secretion of IL-2, interferon-γ, IL-12 and TNF-α, and Th2 by the secretion of IL-4, IL-5, IL-9, IL-10 and IL-13. Nevertheless, these are not strict subsets as IFN-γ and IL-10 can suppress effects associated with Th1 as well as Th2 responses, and IL-4 and IL-13 are also able to promote the production of IL-12, thereby promoting Th1 and potentially inhibiting Th2 responses. Th1 T cells are able to mediate macrophage activation and delayed-type hypersensitivity (DTH), giving rise to pro-inflammatory or cell-mediated immune responses, whereas Th2 T cells promote IgG1 and IgE secretion leading to immediate-type hypersensitivity reactions (humoral immunity; stimulate antibody-mediated responses, activate mast cells, and elicit tissue eosinophilia). Th1 is a key feature in the pathogenesis of diseases like rheumatoid arthritis, sarcoidosis, and tuberculosis, whereas Th2 is involved in allergy, antiparasite responses and in the asthmatic airway (e.g. role in fibrosis).

A non-limitative list of disorders where a medicament or a pharmaceutical composition comprising a soluble protein comprising a sequence having at least 85% of homology with the mature form of the extracellular domain of human CD164 (SEQ ID NO: 1) can be used, includes: multiple sclerosis, systemic lupus erythematosus, rheumatoid arthritis, juvenile idiopathic arthritis, psoriatic arthritis, osteoarthritis, spondylarthropathies, inflammatory bowel disease, endotoxemia, Crohn's disease, Still's disease, uveitis, Wegener's granulomatosis, Behcet's disease, scleroderma, Sjogren's syndrome, sarcoidosis, pyoderma gangrenosum, polymyositis, dermatomyositis, myocarditis, psoriasis, systemic sclerosis, hepatitis C, allergies, allergic inflammation, allergic airway inflammation, chronic obstructive pulmonary disease (COPD), mesenteric infarction, stroke, ulcerative colitis, allergic asthma, bronchial asthma, mesenteric infarction, stroke, fibrosis, post-ischemic inflammation in muscle, kidney and heart, skin inflammation, glomerulonephritis, juvenile onset type I diabetes mellitus, hypersensitivity diseases, viral or acute liver diseases, alcoholic liver failures, tuberculosis, septic shock, HIV-infection, graft-versus-host disease (GVHD) and atherosclerosis.

Rheumatoid arthritis is a disease marked by signs and symptoms of inflammation of the joints. Systemic lupus erythematosus (SLE) is characterized by red, scaley patches on the skin and by malfunction of the kidneys at the advanced stage of the disease, and is associated with inflammatory reactions triggered by deposition of immune complexes in blood vessels, particularly in the kidneys. Multiple sclerosis is a human illness characterized by relapsing, inflammatory conditions that can cause weakness, body tremors and, in extreme cases, paralysis, and is associated with immune system attack of the protective myelin sheath surrounding peripheral nerve cells. Allergic inflammation is consistent with a Th2-cell-based aetiology of atopic disease. For example, defective priming of Th2 cells in the absence of IL-4 resulted in a failure to generate allergic inflammatory responses after subsequent airway challenge. IL-5 and IL-13 have been shown to be more directly responsible for the characteristic eosinophil infiltrates and mucus hypersecretion.

In multiple sclerosis, Th1 mediated immune responses are thought to promote the disease, whereas Th2 mediated immune responses are believed to have an ameliorating effect on the progression of the disease. T cells expressing IL-10 have been shown to suppress experimental autoimmune encephalomyelitis (EAE), a rat model for multiple sclerosis. TNF-α has been hypothesized to be responsible for the induction of EAE (TNF-α can be secreted by both Th1 and Th2 cultures).

Human systemic lupus erythematosus (SLE) is considered to be driven by a Th2 response. However, IFN-γ has been shown to have a major effect on disease progression in a mouse model, whereas IL-4 is expected to mediate disease maintenance.

Myocarditis is defined by inflammation of the heart muscle and is thought to be mediated by an autoimmune response to a cardiac-specific antigen after an acute upper respiratory infection. The severity of the experimental autoimmune myocarditis (EAM) in the mouse model is reduced by administration of anti-IL-4, indicating a role of IL-4 in disease progression.

A further embodiment of the invention is a method of inhibiting the expression of one or more cytokines in an individual comprising administering to said individual a composition comprising a soluble protein comprising a sequence having at least 85% of homology with the mature form of the extracellular domain of human CD164 (SEQ ID NO: 1). The cytokine can be TNF-α, IFN-γ, IL-2, IL-4, IL-5, or IL-10. These methods comprise providing or administering to individuals in need thereof said pharmaceutical or physiologically acceptable composition as described below, and can be considered as methods for preventing and/or treating inflammation and/or autoimmune disorders.

Still another embodiment of the present invention is represented by pharmaceutical compositions comprising a soluble protein comprising a sequence having at least 85% of homology with the mature form of the extracellular domain of human CD164 (SEQ ID NO: 1), in the presence of one or more pharmaceutically acceptable excipients, for the treatment of inflammation and/or autoimmune disorders. These compositions can further comprise an additional immunosuppressant or anti-inflammatory substance. Alternatively, the pharmaceutical compositions comprising the soluble can be combined into a "cocktail" for use in the various treatment regimens.

The pharmaceutical compositions of the invention may also contain any suitable pharmaceutically acceptable carriers, biologically compatible vehicles and additives that are suitable for administration to an animal (for example, physiological saline) and eventually comprising auxiliaries (like excipients, stabilizers or diluents) that facilitate the processing of the active compounds into preparations that can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Cleland J L et al., Curr Opin Biotechnol, 12: 212-9, 2001; Luo B and Prestwich G D, Exp Opin Ther Patents, 11: 1395-1410, 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Any accepted mode of administration can be used and determined by those skilled in the art to establish the desired blood levels of the active ingredients. For example, administration may be by various parenteral routes such as subcutaneous, intravenous, epidural, topical, intradermal, intrathecal, direct intraventricular, intraperitoneal, transdermal (e.g. in slow release formulations), intramuscular, intraperitoneal, intranasal, intrapulmonary (inhaled), intraocular, oral, or buccal routes. Parenteral administration can be by bolus injection or by gradual perfusion over time. Other particularly preferred routes of administration are aerosol and depot formulation. Sustained release formulations, particularly depot, of the invented medicaments are expressly contemplated.

Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions that can be administered rectally include suppositories.

For parenteral (e.g. intravenous, subcutaneous, intramuscular) administration, the active protein(s) can be formulated as a solution, suspension, emulsion or lyophilised powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques. For transmucosal administration, penetrants appropriate to the barrier to be permeated are used in the formulation. Such penetrants are generally known in the art.

Pharmaceutical or physiologically acceptable preparations that can be taken orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner. For administration by inhalation, the compounds for use according to the present invention are conveniently delivered in the form of an aerosol spray presentation from pressurized packs or a nebulizer, with the use of a suitable gaseous propellant, e.g., carbon dioxide. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in aqueous vehicles, and may contain formulatory agents such as suspending, stabilizing and/or dispersing agents. Alternatively, the active ingredient may be in powder or lyophilized form for constitution with a suitable vehicle, such as sterile pyrogen-free water, before use.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight or more. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

An "effective amount" refers to an amount of the active ingredients that is sufficient to affect the course and the severity of the disease, leading to the reduction or remission of such pathology. The effective amount will depend on the route of administration and the condition of the patient.

Dosage intervals can also be determined using the value for the minimum effective concentration. Compounds should be administered using a regimen that maintains plasma levels above the minimum effective concentration for 10-90% of the time, preferably between 30-90%; and most preferably between 50-90%. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician. The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

The substances of the invention may be administered daily or every other day, of less frequent. Preferably, one or more of the substances of the invention are administered one, twice or three times per week. The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

According to the invention, the substances of the invention can be administered prophylactically or therapeutically to an individual prior to, simultaneously or sequentially with other therapeutic regimens or agents (e.g. multiple drug regimens), in a therapeutically effective amount. Active agents that are administered simultaneously with other therapeutic agents can be administered in the same or different compositions.

For any compound used in the method of the invention, the therapeutically effective dose can be estimated initially from cell culture assays. For example, a dose can be formulated in animal models to achieve a circulating concentration range that includes or encompasses a concentration point or range shown to decrease cytokine expression in an in vitro system. Such information can be used to more accurately determine useful doses in humans. A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the LD50, (the dose lethal to 50% of the test population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50, with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, in "The Pharmacological Basis of Therapeutics", Ch. 1).

The present invention provides also provides novel screening assays and kits including soluble proteins comprising a sequence having at least 85% of homology with the mature form of the extracellular domain of human CD164 (SEQ ID NO: 1), that can be used identify and compare the properties of compounds as inhibitors of cytokine secretion and expression. The kits and the assays should comprise a soluble proteins comprising a sequence having at least 85% of homology with the mature form of the extracellular domain of human CD164 (SEQ ID NO: 1), eventually labelled or immobilised on a solid support.

The following definitions are set forth to illustrate and define the meaning and scope of the terms used to describe the invention herein.

As used interchangeably herein, the terms "oligonucleotides", and "polynucleotides" and nucleic acid include RNA, DNA, or RNA/DNA hybrid sequences of more than one nucleotide in either single chain or duplex form. The terms encompass "modified nucleotides" which comprise at least one modification, including by way of example and not limitation: (a) an alternative linking group, (b) an analogous form of purine, (c) an analogous form of pyrimidine, or (d) an analogous sugar. Examples of analogous linking groups, purines, pyrimidines, and sugars are known in the prior art (WO 95/04064). The polynucleotides encoding the soluble proteins may be prepared by any known method, including synthetic, recombinant, ex vivo generation, or a combination thereof, as well as utilizing any purification methods known in the art.

The terms polynucleotide construct, recombinant polynucleotide and recombinant polypeptide are used herein consistently with their use in the art. The terms "upstream" and "downstream" are also used herein consistently with their use in the art. The terms "base paired" and "Watson & Crick base paired" are used interchangeably herein and consistently with their use in the art. Similarly, the terms "complementary", "complement thereof", "complement", "complementary polynucleotide", "complementary nucleic acid" and "complementary nucleotide sequence" are used interchangeably herein and consistently with their use in the art.

Similarly, the term "purified" is used herein to describe a soluble protein that has been separated from other compounds including, but not limited to, nucleic acids, lipids, carbohydrates and other proteins. In some preferred embodiments, a polypeptide is substantially pure when at least about 50%, 60%, 75%, 85%, 90%, 95%, 96%, 97%, 98%, 99%, or 99.5% of the polypeptide molecules of a sample have a single amino acid sequence. In some preferred embodiments, a substantially pure polypeptide typically comprises about 50%, 60%, 70%, 80%, 90% 95%, 96%, 97%, 98%, 99% or 99.5% weight/weight of a protein sample. Polypeptide purity or homogeneity is indicated by a number of methods well known in the art, such as agarose or polyacrylamide gel electrophoresis of a sample, followed by visualizing a single polypeptide band upon staining the gel. For certain purposes, higher resolution can be achieved by using HPLC or other methods well known in the art.

Further, as used herein, the term "purified" does not require absolute purity; rather, it is intended as a relative definition. Purification of starting material or natural material to at least one order of magnitude, preferably two or three orders, and more preferably four or five orders of magnitude is expressly contemplated. Alternatively, purification may be expressed as "at least" a percent purity relative to heterologous polynucleotides (DNA, RNA or both) or polypeptides. As a preferred embodiment, the CD164 polynucleotides or polypeptides are at least; 10%, 20%, 30%, 40%, 50%, 60%, 70%, 80%, 90%, 95%, 96%, 96%, 98%, 99%, 99.5% or 100% pure relative to heterologous polynucleotides or polypeptides. As a further preferred embodiment the polynucleotides or polypeptides have an "at least" purity ranging from any number, to the thousandth position, between 90% and 100% (e.g., at least 99.995% pure) relative to heterologous polynucleotides or polypeptides. Additionally, purity of the polynucleotides or polypeptides may be expressed as a percentage (as described above) relative to all materials and compounds other than the carrier solution. Each number, to the thousandth position, may be claimed as individual species of purity.

The term "isolated" requires that the material be removed from its original environment (e.g., the natural environment if it is naturally occurring). For example, a naturally occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that the vector or composition is not part of its natural environment.

The term "primer" denotes a specific oligonucleotide sequence that is complementary to a target nucleotide sequence and used to hybridize to the target nucleotide sequence. A primer serves as an initiation point for nucleotide polymerization catalyzed by DNA polymerase, RNA polymerase, or reverse transcriptase.

The terms "protein" or "polypeptide" refer to a polymer of amino acids without regard to the length of the polymer. Thus, peptides, oligopeptides, and proteins are included within the definition of polypeptide. This term also does not specify or exclude post-expression modifications of polypeptides. For example, polypeptides that include the covalent attachment of glycosyl groups, acetyl groups, phosphate groups, lipid groups, myristoylated groups and the like are expressly encompassed by the term polypeptide. Also included within the definition are phosphorylated or dephosphorylated polypeptides. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The terms "comprising", "consisting of" and "consisting essentially of" are defined according to their standard meaning. A defined meaning set forth in the M.P.E.P. controls over a defined meaning in the art and a defined meaning set forth in controlling Federal Circuit case law controls over a meaning set forth in the M.P.E.P. With this in mind, the terms may be substituted for one another throughout the instant application in order to attach the specific meaning associated with each term.

The term "treating" as used herein refers to administering a compound after the onset of clinical symptoms.

The term "preventing" as used herein refers to administering a compound before the onset of clinical symptoms.

The term "prevention" within the context of this invention refers not only to a complete prevention of the disease or one or more symptoms of the disease, but also to any partial or substantial prevention, attenuation, reduction, decrease or diminishing of the effect before or at early onset of disease.

The term "treatment" within the context of this invention refers to any beneficial effect on progression of disease, including attenuation, reduction, decrease or diminishing of the pathological development after onset of disease.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The invention will now be described by means of the following Examples, which should not be construed as in any way limiting the present invention. The Examples will refer to the specified Figures.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, and without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Cloning, High Throughput Expression, and Purification in Mammalian Cells Of the His-Tagged, sf-CD164

The cDNA sequence encoding the full extracellular region of human CD164 (residues 1-163 of NCBI Acc. No. NP_006007; SEQ ID NO: 3) was subcloned to generate an expression plasmid using Gateway™ cloning technology (Invitrogen). This expression plasmid allows the expression and the secretion of the mature form of the extracellular region of human CD164 (140 amino acids) as a soluble fusion protein having an hexa-histidine tag fused its C-terminus (146 amino acids; sf-CD164; SEQ ID NO: 2), then used for affinity purification. The secretion is driven by the natural CD164 signal sequence (residues 1-23 of NCBI Acc. No. NP_006007; SEQ ID NO: 3).

The mammalian cells chosen for the high throughput expression were Human Embryonic Kidney 293 cells expressing the Epstein-Barr virus Nuclear Antigen (HEK293-EBNA, Invitrogen).

The cells were maintained in suspension in Ex-cell VPRO serum-free medium (seed stock, maintenance medium, JRH Biosciences). Sixteen to 20 hours prior to transfection (transfection day −1), cells were seeded (density of $2\times10^5$ cells/ml) in 2× T225 flasks, each containing 50 ml DMEM (Dulbecco's modified Eagle's medium)/F12 (1:1) with 2% FBS (fetal bovine serum) seeding medium (JRH Biosciences). The next day (transfection day 0) the transfection took place by using the JetPEI™ reagent (2 µl/µg plasmid; PolyPlus-transfection). For each flask, 113 µg of the sf-CD164 expression plasmid were co-transfected with 2.3 µg of a plasmid expressing Green Fluorescent Protein (GFP). The transfection mix was then added to the 2×T225 flasks and incubated at 37° C. (5% $CO_2$) for 6 days. Confirmation of positive transfection was done by microscopy (Axiovert 10 Zeiss) at day 1 and day 6 for qualitatively evaluating the fluorescence due to GFP. On day 6 (harvest day), supernatants (100 ml) from the two flasks were pooled and centrifuged (4° C., 400 g) and placed into a pot bearing a unique identifier.

The purification process was performed starting from 100 and 500 ml culture medium samples from cells expressing the C-terminal His-tagged recombinant protein. The samples were diluted with one volume cold buffer A (50 mM $NaH_2PO_4$; 600 mM NaCl; 8.7% (w/v) glycerol, pH 7.5) to final volumes of 200 and 1000 ml, respectively. The samples were filtered through a 0.22 µm sterile filter (Millipore, 500 ml filter unit) and kept at 4° C. in sterile square media bottle (Nalgene).

The purification was performed at 4° C. on the VISION workstation (Applied Biosystems) connected to an automatic sample loader (Labomatic). The purification procedure was composed of two sequential steps, metal affinity chromatography on a Poros 20 MC (Applied Biosystems) column charged with Ni ions (4.6×50 mm, 0.83 ml), followed by gel filtration on a Sephadex G-25 medium (Amersham Pharmacia) column (1.0×10 cm).

For the first chromatography step the metal affinity column (Ni-column) was regenerated with 30 column volumes of EDTA solution (100 mM EDTA; 1 M NaCl; pH 8.0), recharged with Ni ions through washing with 15 column volumes of a 100 mM $NiSO_4$ solution, washed with 10 column volumes of buffer A, followed by 7 column volumes of buffer B (50 mM $NaH_2PO_4$; 600 mM NaCl; 8.7% (w/v)

glycerol, 400 mM; imidazole, pH 7.5), and finally equilibrated with 15 column volumes of buffer A containing 15 mM imidazole. The sample was transferred, by the Labomatic sample loader, into a 200 ml sample loop and subsequently charged onto the Ni metal affinity column at a flow rate of 10 ml/min. For the 1000 ml sample the charging procedure was repeated 5 times. The Ni-column was washed with 12 column volumes of buffer A, followed by 28 column volumes of buffer A containing 20 mM imidazole. During this wash, loosely attached contaminating proteins were eluted of the column. The recombinant His-tagged protein was finally eluted from Ni-column with 10 column volumes of buffer B at a flow rate of 2 ml/min, and the eluted protein was collected in a 1.6 ml fraction.

For the second chromatography step, the Sephadex G-25 gel-filtration column was regenerated with 2 ml of buffer D (1.137 M NaCl; 2.7 mM KCl; 1.5 mM $KH_2PO_4$; 8 mM $Na_2HPO_4$; pH 7.2), and subsequently equilibrated with 4 column volumes of buffer C (137 mM NaCl; 2.7 mM KCl; 1.5 mM $KH_2PO_4$; 8 mM $Na_2HPO_4$; 20% (w/v) glycerol; pH 7.4). The peak fraction eluted from the Ni-column was automatically, through the integrated sample loader on the VISION, loaded onto the Sephadex G-25 column and the protein was eluted with buffer C at a flow rate of 2 ml/min. The desalted sample was recovered in a 2.2 ml fraction. The fraction was filtered through a 0.22 μm sterile centrifugation filter (Millipore), aliquoted, frozen and stored at −80° C. An aliquot of the sample was analyzed on SDS-PAGE (4-12% NuPAGE gel; Novex) by Coomassie staining and Western blot with anti-His antibodies.

Coomassie staining was performed by incubating the NuPAGE gel in a 0.1% Coomassie blue R250 staining solution (30% methanol, 10% acetic acid) at room temperature for 1 hour. The gel was subsequently destained in 20% methanol, 7.5% acetic acid until the background was clear and the protein bands clearly visible.

For the Western blot, the proteins were electrotransferred from the NuPAGE gel to a nitrocellulose membrane at 290 mA for 1 hour at 4° C. The membrane was blocked with 5% milk powder in buffer E (137 mM NaCl; 2.7 mM KCl; 1.5 mM $KH_2PO_4$; 8 mM $Na_2HPO_4$; 0.1% Tween 20, pH 7.4) for 1 hour at room temperature, and subsequently incubated with a mixture of 2 rabbit polyclonal anti-His antibodies (G-18 and H-15, 0.2 ug/ml each; Santa Cruz) in 2.5% milk powder in buffer E overnight at 4° C. After further 1 hour incubation at room temperature, the membrane was washed with buffer E (3×10 min), and then incubated with a secondary HRP-conjugated anti-rabbit antibody (DAKO, HRP 0399) diluted 1/3000 in buffer E containing 2.5% milk powder for 2 hours at room temperature. After washing with buffer E (3×10 minutes), the membrane was developed with the ECL kit (Amersham Pharmacia) for 1 min. The membrane was subsequently exposed to a Hyperfilm (Amersham Pharmacia), the film developed and the western blot image visually analyzed.

The protein concentration in the samples was determined using the BCA protein assay kit (Pierce) with bovine serum albumin as standard.

Example 2

Effect of sf-CD164 on Cytokine Release Measured by Cell-Based Assays

The following in vitro cell-based assays measure the effects of sf-CD164 on cytokine secretion induced by Concanavalin A (Con A) as measured by a cytokine bead array (CBA) assay for IL-2, IFN-γ, TNF-α, IL-5, IL-4 and IL-10.

The following equipments and software were used:
96 well microtiter plate photometer EX (Labsystem).
Graph Pad Software (Prism)
Excel software (Microsoft)
Flow cytometer (Becton-Dickinson)
CBA Analysis software
Hood for cell culture
Incubator for cell culture
Centrifuge
Pipettes
The following materials and reagents were used:
Buffy coat
DMEM (GIBCO)
Human serum type AB (SIGMA)
L-Glutamine (GIBCO)
Penicillin-Streptomycin (GIBCO)
Ficoll (PHARMACIA)
96 well microtiter plate for cell culture (COSTAR)
Concanavalin A (SIGMA)
Human Th1/Th2 Cytokine CBA Kit (Becton-Dickinson)
PBS (GIBCO)
Falcon 50 ml sterile tubes (Becton-Dickinson)
Bovine Serum Albumin (BSA; SIGMA)
Glycerol (MERCK)
Dimethyl Sulfoxide (DMSO; SIGMA)
96 well microtiter plate conical bottom (NUNC)
autoMACS™ Separator and MACS cell isolation kit (Miltenyl Biotec)

The cells were isolated for cell-based assays as follows.

Human peripheral blood mononuclear cells (PBMC) were isolated from buffy coat diluted with DMEM. 25 ml of diluted blood was thereafter slowly added onto a 15 ml layer of Ficoll in a 50 ml Falcon tube, and tubes were centrifuged (2000 rpm, 20 minutes, at Room Temperature without brake). The interphase (ring) was then collected and the cells were washed with 25 ml of DMEM followed by a centrifuge step (1200 rpm, 5 min). This procedure was repeated three times. A buffy coat gave approximately $600 \times 10^6$ total cells.

Sub-populations of leukocytes (T cells, B cells, Monocytes) were prepared from PBMC according to the isolation kit manufacturer's instruction (MACS; Miltenyl Biotec). PBMC were isolated from buffy coats as described above. Care was taken to ensure a single-cell suspension. For preparation of CD4+ T cells, the CD4+ T Cell Isolation Kit II was used (catalogue number 130-091-155, Miltenyl Biotec). PBMC were counted, centrifuged for 10 minutes and re-suspended in cold PBS buffer (phosphate buffered saline pH 7.2, supplemented with 0.5% BSA, and 2 mM EDTA) at a concentration of $2.5 \times 10^8$ cells per ml (40 μl of buffer per $10^7$ cells). 10 μl of Biotin-Antibody Cocktail (supplied with the kit) per $10^7$ total cells was added. The suspension was mixed well and incubated at 4-8° C. for 10 minutes. 30 μl of buffer was added per $10^7$ cells followed by 20 μl of Anti-Biotin MicroBeads per $10^7$ total cells. The suspension was mixed well and incubated for an additional 15 minutes at 4-8° C. The cells were washed with buffer by adding 10-20× the labeling volume and centrifuged at 300×g for 10 minutes. The supernatant was removed completely and the cells re-suspended up to $10^8$ cells in 500 μl of buffer. Magnetic separation was carried out with an autoMACS™ Separator. The autoMACS™ Separator was prepared and primed according to the manufacturer's instructions. The tube containing the magnetically labeled cells was placed in the autoMACS™ Separator and the program "deplete" was chosen, The negative fraction was collected (outlet port "neg1"). This fraction represents the enriched CD4+ T cells. Where required, the positive fraction was subsequently collected (outlet port "pos1"). This fraction represents the magnetically labeled non-CD4+ T cells.

The conditions applied for the cell-based assays were the following:
- 100 000 cells/well in 96-well plates in 100 μl final in 2% glycerol.
- 5 ng/ml of the mitogen Concanavallin A (ConA).
- 48 hours for each assay.

The cells were prepared in each well by mixing
- 80 μl of 1.25×10$^6$ cells/ml were diluted in DMEM+2.5% Human Serum+1% L-Glutamine+1% Penicillin-Streptomycin.
- 10 μl of the solution containing sf-CD164 that was diluted in PBS+20% Glycerol (the final dilution of the proteins is 1/10);
- 10 μl ConA.

After 48 hours, cell supernatants were collected and human cytokines were measured by Human Th1/Th2 Cytokine CBA Kit (Becton-Dickinson).

The mixed Human Th1/Th2 Capture Beads suspension were prepared by vigorously vortexing for a few seconds before mixing with the samples from microwell plate. For each assay to be analysed, 10 μl aliquot of each capture bead were added into a single tube labelled "mixed capture beads". The Bead mixture was thoroughly vortexed. The supernatants were diluted (1:4) using the Assay Diluent (20 μl of supernatants+60 μl of Assay Diluent). The sample dilution was then mixed before transferring samples into a 96 wells microtiter plate conical bottom (Nunc).

The human Th1/Th2 Cytokine CBA Assay was performed by adding 50 μl of the diluted supernatants into a 96 wells microtiter plate conical bottom (Nunc). 50 μl of the mixed capture beads were added followed by 50 μl addition of the Human Th1/Th2 PE Detection Reagent. The plate was then incubated for 3 hours at RT and protected from direct exposure to light followed by centrifugation at 1500 rpm for 5 minutes. The supernatant was then carefully discarded. In a subsequent step, 200 μl of wash buffer were twice added to each well, centrifuged at 1500 rpm for 5 minutes and supernatant carefully discarded. 130 μl of wash buffer were thereafter added to each well to resuspend the bead pellet. The samples were finally analysed on a flow cytometer. The data were analysed using the CBA Application Software, Activity Base and Microsoft Excel software.

The effect of sf-CD164 on cytokine release from human PBMC cells (mixture) and isolated T cells was measured for six cytokines: TNF-α, IFN-γ, IL-2, IL-4, IL-5 and IL-10. The release of these cytokines was significantly diminished and in a dose dependent manner by sf-CD164 in both cell-based assays (IC50 are summarized in Table III). Two exemplary dose-dependent curves are shown for IL-2 and TNF-α for both human PBMC and isolated CD4+ T cells in FIGS. 2 and 3, respectively.

Example 3

Effect of sf-CD164 Administration on Cytokine Release Measured in the LPS Induced TNF-α Release Animal Model The model of lipopolysaccharide (LPS)-induced TNF-α release in mice was set up according the patent WO98/38179. LPS (O111:B4; SIGMA) was injected (0.3 mg/kg, i.p.) in C3H/HeN mice (Charles River, France). Ninety minutes later blood was sampled and plasma TNF-α was determined using an ELISA kit (R&D). Sf-CD164 and dexamethasone were diluted in PBS and injected (Sf-CD164 at 0.03, 0.1 and 0.3 mg/kg, iv; or dexamethasone at 0.1 mg/kg, sc) 15 minutes prior to LPS administration.

Dexamethasone, the anti-inflammatory compound used as positive control significantly (p<0.001) inhibited LPS-induced TNF-α release by 72%. Sf-CD164, at 0.3 mg/kg, significantly (p<0.01) inhibited LPS-induced TNF-α release by 38% (FIG. 4). The lower doses of 0.03 and 0.1 mg/kg were capable to inhibit TNF-α but in a manner less significant statistically.

Example 4

Effect of sf-CD164 Administration on Immune Cells Recruitment Measured in Two Animal Models The effect of sf-D 164 administration on immune cells recruitment was first tested using the thyoglicollate-induced leukocyte peritoneal recruitment assay (FIG. 5).

The mice (strain C3H, 8 week old, n=6; Elevage Janvier, France) were injected with sf-CD164 (0.03, 0.1 and 0.3 mg/kg, iv) or dexamethasone (1 mg/kg, sc) diluted in PBS containing 0.02% BSA. Thioglycollate (1.5%, 40 ml/kg, ip; SIGMA) was injected 15 minutes after administration of the test molecules. A second administration of the test molecules was done 24 hours later. Forty-eight hours after the challenge with thioglycollate, the animals were sacrificed and the lavage of the peritoneal cavity was conducted using 2×5 ml PBS-1 mM EDTA (+4° C.). After centrifugation (10 min at 3000 rpm), the pellet was resuspended in 1 ml PBS. The peritoneal cells were counted using a Beckman/Coulter counter.

Dexamethasone inhibited significantly (p<0.001) the recruitment of macrophages by 69%. This effect was on a dose dependent manner. Sf-CD164 (0.03, 0.1 and 0.3 mg/kg) significantly inhibited thioglycollate-induced peritoneal recruitment of macrophages by 5%, 26% (p<0.05) and 43% (p<0.001), respectively, as well as lymphocytes (by 14%, 18% and 34% respectively) and neutrophils peritoneal recruitment (by 3%, 9% and 23% respectively).

Similar results were obtained in the LPS-induced peritoneal recruitment of neutrophils and lymphocytes (FIG. 5).

The same administration protocol described above was used with LPS (O111:B4, Sigma; 0.9 mg/kg, 40 ml/kg, ip). Sf-CD164 (0.03, 0.1 and 0.3 mg/kg) significantly inhibited LPS-induced peritoneal recruitment of neutrophils by 9%, 35% (p<0.001) and 43% (p<0.001), respectively. At the same doses it also significantly inhibited the recruitment of activated lymphocytes by 8%, 26% (p<0.05) and 47% (p<0.001), respectively. Dexamethasone (0.1 mg/kg) significantly (p<0.001) inhibited the recruitment of activated lymphocytes.

Example 5

Effect of sf-CD164 in a Cell-Based Assay for MBP-Specific Antigen Processing and Presentation An assay was developed to test the effect of sf-CD164 on the proliferation of myelin basic protein (MBP)-specific T cells induced by myelin basic protein peptide Ac1-11 (MBP (Ac1-11)). It has been shown that epicutaneous immunization (ECi) with the immunodominant peptide of myelin basic protein (MBP), Ac1-11, protects mice that are transgenic for an Ac1-11-specific T cell receptor against both the induced and spontaneous forms of experimental allergic encephalomyelitis (EAE).

Spleens from B10.PL and MBP transgenic mice were harvested and homogenized to obtain single cell suspensions. After erythrocyte lysis with the Gay's solution, splenocytes were resuspended in PBS, washed and counted. After the isolation procedures, cellular viability was more than 90% by trypan blue dye exclusion. The B10.PL antigen presenting cells (APCs) were then irradiated with 25 Gy of g-irradiation (stimulants), washed and resuspended incomplete medium at $1.9*10^6$ cells/ml. The responder cell population was adjusted at $3.8*10^6$ cells/ml in complete medium. 80 µl of each cell suspension per well was mixed in 96 well plates. The antigen was then added in a volume of 20 µl: 10 g/ml of MBP murine or 1 µg/ml of Ac 1-11 MBP peptide per well (adequate negative controls are BSA, MSA and an irrelevant MBP-derived peptide respectively). The proteins or small molecules were added in a volume of 20 µl and then incubated at 37° C. in a humidified atmosphere with 5% CO2. After 3 days of culture, either the supernatants were harvested and freezed at −80° C. until testing for cytokine production or 1 µCi of $^3$H thymidine was added and counted for radioactivity incorporation after 14-16 hours of additional incubation.

Figure 6:
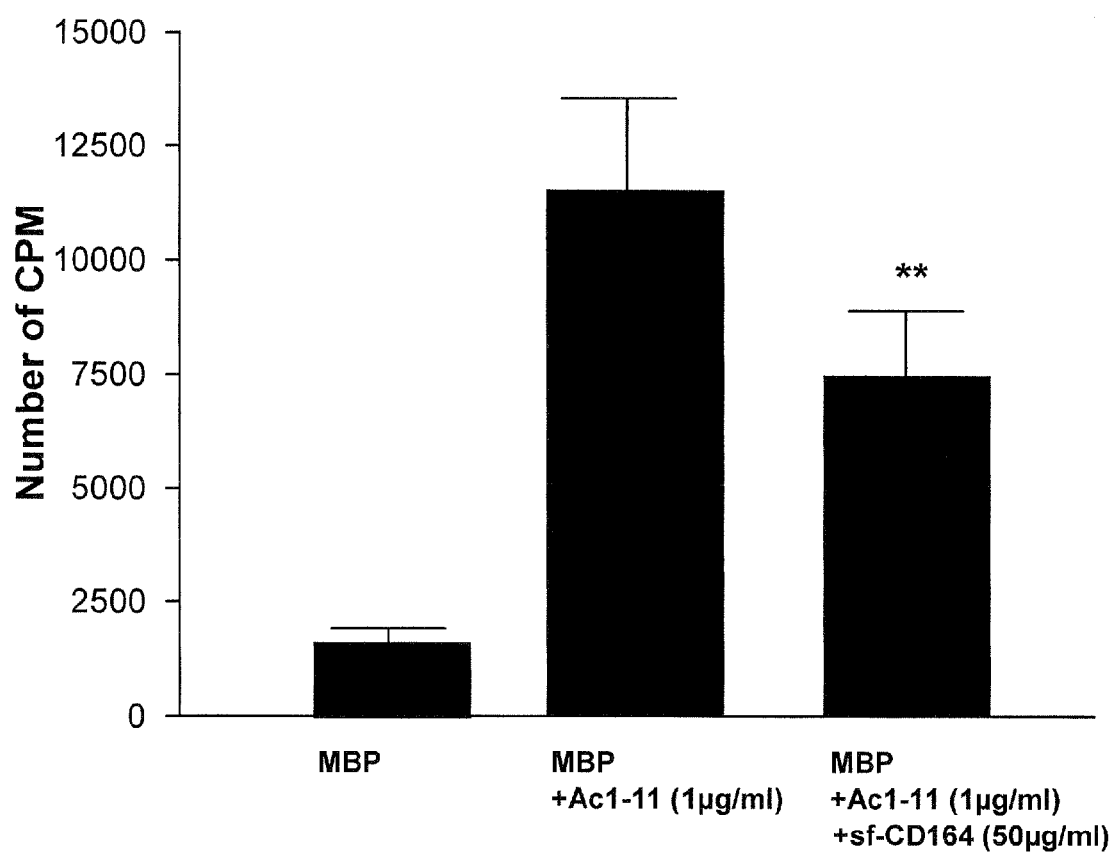
FIG. 6: effect of sf-CD164 administration on the proliferation of autoantigenic MBP specific T cells. The Y-axis represents the radioactivity (CPM, counts per minute) related to the incorporation of radiolabeled nucleotides ($^3$H thymidine) by dividing cells. The asterisks indicate the statistical significance.

Sf-CD164 (50 µg/ml) significantly inhibited the proliferation of MBP specific T cells induced by Ac1-11 (1 µg/ml; FIG. 6). Thus, sf-CD164 or soluble CD164 might be useful in the treatment of multiple sclerosis.

Example 6

Effect of sf-CD164 Administration in an Animal Model of Fulminant Liver Hepatitis Sf-CD164 protein has been shown in vitro to inhibit secretion of certain cytokines by ConA-stimulated human peripheral blood mononuclear cells (PBMC). Since cytokines play a crucial role in T cell induced ConA induced liver hepatitis (Seino et al. 2001, Annals of surgery 234, 681; Kusters S, Gastroenterology 111(2):462-71, 1996; Toyonaga et al. 1994, PNAS 91, 614-618), we tested sf-CD164 in this model.

Female C57/BL6 mice (8 weeks of age; IFFA CREDO) were used. In general, 7 animals per experimental group are used. Mice were maintained in standard conditions under a 12-hour light-dark cycle, provided irradiated food and water ad libitum.

Concanavallin A (ConA; Sigma ref.C7275) was injected at 18 mg/kg iv and blood samples were taken at 1.30 and 8 hours post-injection. Sf-CD164 was injected 30 minutes before ConA injection. Positive controls were injected with Dexamethasone (0.1 mg/kg), and negative control were injected with PBS-BSA 1.8% glycerol. At the time of sacrifice, blood was taken from the heart. IL-6 and IFN-gamma cytokine levels were measured using the TH1/TH2 CBA assay 1.5 hours after ConA injection. Transaminase blood parameters were determined using the COBAS instrument (Hitachi).

Figure 7:
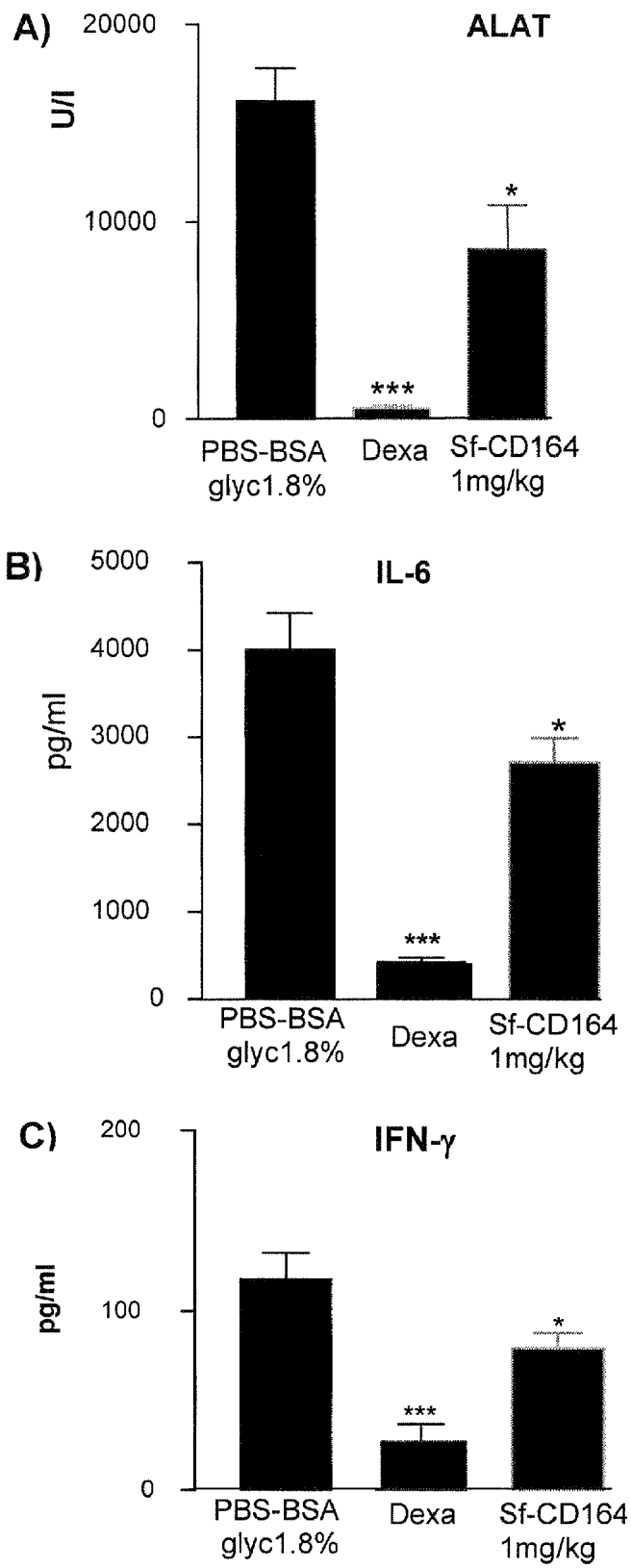
FIG. 7: effect of sf-CD164 administration to the ConA-induced hepatitis animal model on transaminase levels (ALAT; A) IL-6 release (B), and IFN-γ (C) release. Dexa stands for Dexamethasone. The asterisks indicate the statistical significance.

The experiment shows that sf-CD164 (1 mg/kg) protects from liver injury in a mouse model mimicking fulminant hepatitis after subcutaneous delivery of sf-CD164, since it decreases relevant parameters such as transaminases levels (ALAT), IFN-γ, and IL-6 cytokine levels (FIG. 7). The decrease in ALAT levels might be due to both decreased IFN-γ and IL-6 levels. Different cytokines have been involved in the liver damage after ConA injection. For example, anti TNF-alpha antibodies confer protection against disease (Seino et al. 2001, Annals of surgery 234, 681) and inhibition of IL-4 production by NKT cells was shown to be hepatoprotective in T-cell mediated hepatitis in mouse (Ajuebor et al. 2003 J. Immunology 170, 5252-9).

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

TABLE III

| CYTOKINE | IC50 in PBMC | IC50 in CD4+ T CELLS |
|---|---|---|
| TNF-α | 0.66 µg/ml | 1.6 µg/ml |
| IFN-γ | 0.84 µg/ml | 1.6 µg/ml |
| IL-2 | 0.46 µg/ml | 1.2 µg/ml |
| IL-4 | 0.52 µg/ml | 1.5 µg/ml |
| IL-5 | 1.19 µg/ml | 3.3 µg/ml |
| IL-10 | 0.53 µg/ml | 3.0 µg/ml |

I claim:

1. A method of reducing serum transaminase, IFN-γ and IL-6 levels in an individual having fulminant liver hepatitis comprising the administration of a composition comprising a soluble protein comprising SEQ ID NO: 1 to an individual having fulminant liver hepatitis in an amount sufficient to reduce serum transaminase, IFN-γ and IL-6 levels in said individual.

2. The method according to claim 1, wherein said soluble protein is chosen from:
   a) SEQ ID NO: 1; or
   b) SEQ ID NO: 1 fused to the signal sequence of human CD164.

3. The method according to claim 1, wherein said soluble protein is glycosylated.

4. The method according to claim 3, wherein said soluble protein is glycosylated at any of the positions as set forth in SEQ ID NO: 1.

5. The method according to claim 1, wherein said soluble protein is phosphorylated.

6. The method according to claim 5, wherein said soluble protein is phosphorylated at any of the positions as set forth in SEQ ID NO: 1.

7. The method according to claim 1, wherein said soluble protein is myristoylated.

8. The method according to claim 7, wherein said soluble protein is myristoylated at any of the positions as set forth in SEQ ID NO: 1.

9. The method according to claim 1, wherein said soluble protein is a soluble fusion protein.

10. The method according to claim 9, wherein said soluble fusion protein comprises a signal sequence.

11. The method according to claim 9, wherein said soluble fusion protein contains a Histidine tag.

12. The method according to claim 11, wherein said soluble fusion protein is SEQ ID NO: 2.

13. The method according to claim 9, wherein said soluble fusion protein comprises an Fc region of an immunoglobulin.

* * * * *

UNITED STATES PATENT AND TRADEMARK OFFICE
CERTIFICATE OF CORRECTION

| | |
|---|---|
| PATENT NO. | : 8,075,894 B2 |
| APPLICATION NO. | : 12/341490 |
| DATED | : December 13, 2011 |
| INVENTOR(S) | : Yolande Chvatchko |

It is certified that error appears in the above-identified patent and that said Letters Patent is hereby corrected as shown below:

Column 1,
Line 48, "and or/the" should read --and/or the--.

Column 3,
Line 28, "NCBI Ace." should read --NCBI Acc.--.

Column 6,
Line 47, "many example on these" should read --many examples of these--.
Line 52, "18-126" should read --118-126--.

Column 9,
Line 51, "of 1 g" should read --of Ig--.

Column 13,
Line 50, "derived form" should read --derived from--.

Column 16,
Line 33, "cane be" should read --can be--.

Column 19,
Line 57, "(TNF-αcan" should read --(TNF-α can--.

Column 22,
Line 54, "of less frequent." should read --or less frequent.--.

Column 23,
Line 36, "can be used identify" should read --can be used to identify--.

Signed and Sealed this
Twenty-seventh Day of March, 2012

David J. Kappos
*Director of the United States Patent and Trademark Office*

CERTIFICATE OF CORRECTION (continued)
U.S. Pat. No. 8,075,894 B2

Column 24,
Line 14, "90% 95%" should read --90%, 95%--.
Line 32, "96%, 96%, 98%" should read --96%, 97%, 98%--.

Column 30,
Line 7, "TNF-αrelease" should read --TNF-α release--.

Column 31,
Line 12, "10g/ml" should read --10μg/ml--.
Line 49, "control were" should read --controls were--.